(12) United States Patent
Nakahama et al.

(10) Patent No.: US 6,709,837 B1
(45) Date of Patent: Mar. 23, 2004

(54) POLYPEPTIDE AND PRODUCTION THEREOF

(75) Inventors: Kazuo Nakahama, Kyoto (JP); Yoshihiko Kaisho, Osaka (JP); Koji Yoshimura, Osaka (JP); Reiko Sasada, Kyoto (JP)

(73) Assignee: Takeda Chemical Industries, Inc., Osaka (JP)

( * ) Notice: Subject to any disclaimer, the term of this patent is extended or adjusted under 35 U.S.C. 154(b) by 315 days.

(21) Appl. No.: 07/488,696

(22) Filed: Mar. 5, 1990

(30) Foreign Application Priority Data

| Mar. 10, 1989 | (JP) | ................................................ | 1-58983 |
| May 19, 1989 | (JP) | ................................................ | 1-127710 |
| Jul. 26, 1989 | (JP) | ................................................ | 1-193654 |
| Oct. 9, 1989 | (JP) | ................................................ | 1-263613 |

(51) Int. Cl.⁷ .......................... C12N 5/00; C12N 15/12; C07K 14/475
(52) U.S. Cl. ...................... 435/69.1; 530/350; 530/399; 536/23.5; 435/320.1; 435/325; 435/356; 435/252.3; 435/252.33; 435/254.2; 435/254.21
(58) Field of Search .................... 530/399, 350, 530/412; 536/23.51, 23.5; 435/69.1, 320.1, 252.3, 325, 356, 252.33, 254.2, 254.21

(56) References Cited

U.S. PATENT DOCUMENTS 5,180,820 A  *  1/1993  Barde et al. ............. 536/23.51

FOREIGN PATENT DOCUMENTS

EP             0121338       10/1984

OTHER PUBLICATIONS

Maisonpierre et al. *Science* 247:1446–1451 (1990).*
A. Ullrich, et al., Nature, 202:821 (1983).
J. Scott, et al., Nature, 302:538 (1983).
R. Meier, et al., The EMBO Journal, vol. 5, No. 7, pp. 1489–1493 (1986).
J. Leibrock, et al., Nature 341:149 (1989).
Y.A. Barde, et al., The EMBO Journal, vol. 1, No. 5, pp. 549–553 (1982).

* cited by examiner

*Primary Examiner*—Marianne P. Allen
(74) *Attorney, Agent, or Firm*—Edwards & Angell, LLP; David G. Conlin; Dianne M. Rees

(57) ABSTRACT

Disclosed are (1) a polypeptide (I) including the following amino acid sequence (II) in a molecule thereof:

```
TyrAlaGluHisLysSerHisArgGlyGluTyrSerValCys      (II)
AspSerGluSerLeuTrpValThrAspLysSerSerAlaIle
spIleArgGlyHisGlnValThrValLeuGlyGluIleLys
ThrGlyAsnSerProValLysGlnTyrPheTyrGluThrArg
CysLysGluAlaArgProValLysAsnGlyCysArgGlyIle
AspAspLysHisTrpAsnSerGlnCysLysThrSerGlnThr
TyrValArgAlaLeuThrSerGluAsnAsnLysLeuValGly
TrpArgTrpIleArgIleAspThrSerCysValCysAlaLeu
SerArgLysIleGlyArg
```

(2) a DNA sequence coding for the polypeptide described in (1), (3) a vector including the DNA described in (2), (4) a transformant transformed by the vector described in (3), and (5) a process for producing the polypeptide (I) which comprises cultivating the transformant described in (4) in a culture medium to produce and accumulate the polypeptide described in (1) in a culture. The polypeptide is useful as a reagent for studies relating to the differentiation, growth and survival of animal cells, and may also be useful as a drug.

25 Claims, 17 Drawing Sheets

```
                10            20            30            40            50            60
        GATTACGTGGGCAGCCCCGTGGTGGCGAACAGAACATCACGGCGAACGGTACGCGAG
        AspTyrValGlySerProValValAlaAsnArgThrSerArgArgLysArgTyrAlaGlu
                                    -10                        -1  1
                70            80            90           100           110           120
        CATAAGAGTCACCGAGGGGAGTACTCGGTATGTGACAGTGAGAGTCTGTGGGTGACCGAC
        HisLysSerHisArgGlyGluTyrSerValCysAspSerGluSerLeuTrpValThrAsp
                                    10                         20
```

```
           130       140       150       160       170       180
AAGTCATCGGCCATCGACATTCGGGACCACCAGGTCACGGTGCTGGGGAGATCAAAACG
LysSerSerAlaIleAspIleArgGlyHisGlnValThrValLeuGlyGluIleLysThr
                       30                                 40

190       200       210       220       230       240
GGCAACTCTCCCGTCAAACAATATTTTATGAAACGGATGTAAGGAAGCCAGGCCGGTC
GlyAsnSerProValLysGlnTyrPheTyrGluThrArgCysLysGluAlaArgProVal
                       50                                 60

250       260       270       280       290       300
AAAAACGGGTGCAGGGGTATTGATGATAATAAACACTGGAACTCTCAGTGCAAAACATCCAA
LysAsnGlyCysArgGlyIleAspAspLysHisTrpAsnSerGlnCysLysThrSerGln
                       70                                 80

310       320       330       340       350       360
ACCTACGTCCGAGCACTGACTTCAGAGAACAATAAACTCGTGGGCTGGCGGTGATACGG
ThrTyrValArgAlaLeuThrSerGluAsnAsnLysLeuValGlyTrpArgTrpIleArg
                       90                                100

370       380       390       400       410       420
ATAGACACGTCCTGTGTGTGCCTTGTCCGAGAAAATCGGAAGAACATGAATTGGCATC
IleAspThrSerCysValCysAlaLeuSerArgLysIleGlyArgThrEnd
                      110

430       440       450       460       470       480
TCTCCCATATATAAATTATTACTTTAAATTATATGATATGCATGTAGCATATAAATGTT 490       500       510       520       530       540
TATATTGTTTTATATATTATATAAGTTGACCTTTATTTATTAAACTTCAGCAACCCTACAG
```

FIG. 2B

```
                                            TyrAlaGluHisLys
                                            SerSerSerHisPro

Ser----HisArgGlyGluTyrSerValCysAspSer GluSerLeuTrpValThrAspLys
IlePheHisArgGlyGluPheSerValCysAspSer ValSerValTrpValGlyAspLys

SerSerAlaIleAspIleArgGlyHisGlnValThr ValLeuGlyGlyIleLysThrGly
ThrThrAlaThrAspIleLysGlyLysGluValMet ValLeuGlyGluValAsnIleAsn

AsnSerProValLysGlnTyrPheTyrGluThrArg CysLysGluAlaArgProValLys
AsnSerValPheLysGlnTyrPheLysGluThrPhe CysLysCysArgAspProAsnProValAsp

AsnGlyCysArgGlyIleAspLysHisTrpAsnSer GlnCysLysThrSerGlnThr
SerGlyCysArgGlyIleAspSerLysHisTrpAsnSer TyrCysThrThrThrHisThr

TyrValArgAlaLeuThrSerGluAsnAsnLysLeu ValGlyTrpArgIleArgIle
PheValLysAlaLeuThrMetAspGly----LysGln AlaAlaTrpArgPheIleArgIle

AspThrSerCysValCysAlaLeuSerArgLysIle GlyArg----Thr
AspThrAlaCysValCysValLeuSerArgLysLeu SerArgLysAlaValArgArgAla
```

FIG. 3

ATGTCCATCTTGTTTTATGTGATATTTCTGCTTATCTCCGTTGGCATCCAAGGTAACAAC
|MetSerIleLeuPheTyrValIlePheLeuAlaTyrLeuArgGlyIleGlnGly|AsnAsn
└→Signal                                                └→Pro GCCATGGTTACTTTTGCCACGATCTTACAGGTGAACAAGGTG
AlaMetValThrPheAlaThrIleLeuGlnValAsnLysVal ATGGATCAAAGGAGTTTGCCAGAAGACTCGCTCAATTCCCTCATTATTAAGCTGATCCAG
MetAspGlnArgSerLeuProGluAspSerLeuAsnSerLeuIleIleLysLeuIleGln GCAGATATTTTGAAAAACAAGCTCTCCAAGCAGATGGTGGACGTTAAGGAAAAATTACCAG
AlaAspIleLeuLysAsnLysLeuSerLysGlnMetValAspValLysGluAsnTyrGln

FIG. 5A

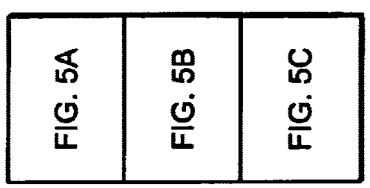

FIG. 5

AGCACCCTGCCCAAAGCTGAGGCTCCCGAGAGCCGGAGCGGGAGGGCCCCAAGTCA
SerThrLeuProLysAlaGluAlaProArgGluProArgGlyGlyProAlaLysSer

GCATTCCAGCCAGTGATTGCAATGGACACCGAACTGCTGCGACAACAGAGACGCTACAAC
AlaPheGlnProValIleAlaMetAspThrGluLeuLeuArgGlnGlnArgArgTyrAsn

SacII
TCACCGCGGGGTCCTGCTGAGCGACAGCACCCCCCTTGAGCCCCGCCCTTGTATCTCATG
SerProArgValLeuLeuSerAspSerThrProLeuGluProProProLeuTyrLeuMet

GAGGATTACGTGGGCAGCCCGTGGTGGCAACAGAACATCACGGCGGAAACGGTACGCG
GluAspTyrValGlySerProValValAlaAsnArgThrSerArgArgLysArg|TyrAla
                                                    →Mature ScaI
GAGCATAAGAGTCACCGAGGGGAGTACTCGGTATGTGACAGTGAGAGTCTCTGTGGGTGACC
GluHisLysSerHisArgGlyGluTyrSerValCysAspSerGluSerLeuTrpValThr GACAAGTCATCGGCCATCGACATTCGGGACACCAGGTCACGGTGCTGGGGGAGATCAAA
AspLysSerSerAlaIleAspIleArgGlyHisGlnValThrValLeuGlyGluIleLys ACGGGCAACTCTCCCGTCAAACAATATTTTATGAAACGCGATGTAAGGAAGCCAGGCCG
ThrGlyAsnSerProValLysGlnTyrPheTyrGluThrArgCysLysGluAlaArgPro

FIG. 5B

GTCAAAAACGGTTGCAGGGTATTGATGATAAACACTGGAACTCTCAGTGCAAACATCC
ValLysAsnGlyCysArgGlyIleAspAspLysHisTrpAsnSerGlnCysLysThrSer

CAAACCTACGTCCGAGCACTGACTTCAGAGAACAATAAACTCGTGGGCTGGCGGTGATA
GlnThrTyrValArgAlaLeuThrSerGluAsnAsnLysLeuValGlyTrpArgTrpIle

CGGATAGACACGTCCTGTGTGTGCCTTGTCGAGAAAAATCGGAAGAACATGAATTGGC
ArgIleAspThrSerCysValCysAlaLeuSerArgLysIleGlyArgThr***

AhaII       NsiI
ATCTCTCCCCATATATAAATTATTACTTTAAATTATATGATATGCATGTAGCATATAAAT

GTTTATATTGTTTTATATATATTATAAGTTGACCTTTATTTATTAAACTTCAGCAACCCTA

CAGTATATAGGCTTTTTTTCTCAATAAAAATCAGTGTGCTTGCCTTCCCCTCAGGCCTCTCCC

ATCTGTTAAAACTTGTTTTTGTGATCCGGCTCTCAGGAGTCACTCTGTAAAATCTGTGTAC

ACCAGTATTTTGCATTCAGTATTGTC

FIG. 5C

```
          10        20        30        40        50        60
AGATCTTACAGGTGAACAAGGTGATGTCCATCTTGTTTTATGTGATATTTCTTGCTTATC
                  MetSerIleLeuPheTyrValIlePheLeuAlaTyrL 70        80        90       100       110       120
TCCGTGGCATCCAAGGCAACAACATGGATCAAAGGAGTTTGCCAGAAGACTCTCTCAATT
euArgGlyIleGlnGlyAsnAsnMetAspGlnArgSerLeuProGluAspSerLeuAsnS 130       140       150       160       170       180
CCCTCATTATCAAGTTGATCCAGGGGATATCTTGAAAAACAAGCTCTCCAAGCAGATGG
erLeuIleIleLysLeuIleGlnAlaAspIleLeuLysAsnLysLeuSerLysGlnMetV
```

FIG. 11A

| FIG. 11A |
|----------|
| FIG. 11B |
| FIG. 11C |

FIG. 11

```
        190              200              210              220              230              240
TAGATGTTAAGGAAAATTACCAGAGAGCACCCTGCCCAAAGCAGAGGCACCCAGAGAACCAG
 aIAspValLysGluAsnTyrGlnSerThrLeuProLysAlaGluAlaProArgGluProG 250              260              270              280              290              300
AGCAGGGAGAGGCCACCAGGTCAGAATTCCAGCCGATGATTGCAACAGACACAGAACTAC
 luGlnGlyGluAlaThrArgSerGluPheGlnProMetIleAlaThrAspThrGluLeuL 310              320              330              340              350              360
TACGGCAACAGAGACGCTACACAATTCACCCCGGGTCCTGCTGAGTGACAGCACCCCTTGG
 euArgGlnArgArgTyrAsnSerProArgValLeuLeuSerAspSerThrProLeuG 370              380              390              400              410              420
AGCCCCTCCCTTATATCTAATGGAAGATTATGTGGGCAACCCGGTGGTAACCAATAGAA
 luProProLeuTyrLeuMetGluAspTyrValGlyAsnProValThrAsnArgT 430              440              450              460              470              480
CATCACCACGGAGGAAACGCTATGCAGAGCATAAGAGTCACCGAGGAGTACTCAGTGT
 hrSerProArgArgLysArgTyrAlaGluHisLysSerHisArgGlyGluTyrSerValC
                     →Mature 490              500              510              520              530              540
GTGACAGTGAGAGCCTGTGGGTGACCGACAAGTCCTCAGCCATTGACATTCGGGGACACC
 ysAspSerGluSerLeuTrpValThrAspLysSerSerAlaIleAspIleArgGlyHisG
```

FIG. 11B

```
        550         560         570         580         590         600
AGGTTACAGTGTTGGGAGAGATCAAAACCGGCAACTCTCCTGTGAAACAATATTTTATG
lnValThrValLeuGlyGluIleLysThrGlyAsnSerProValLysGlnTyrPheTyrG 610         620         630         640         650         660
AAACGAGGTGTAAAGAAGCCAGGCCAGTCAAAAACGGTTGCAGGGGATTGATGACAAAC
luThrArgCysLysGluAlaArgProValLysAsnGlyCysArgGlyIleAspAsnLysH 670         680         690         700         710         720
ACTGGAACTCTCAGTGCAAAACGTCGCAAACCTACGTCCGAGCACTACTTCAGAAAACA
isTrpAsnSerGlnCysLysThrSerGlnThrTyrValArgAlaLeuThrSerGluAsnA 730         740         750         760         770         780
ACAAACTCGTAGGCTGGCGCTGGATACGAATAGACACTTCCTGTGTGTGCCTTGTCAA
snLysLeuValGlyTrpArgTrpIleArgIleAspThrSerCysValCysAlaLeuSerA 790         800         810         820         830         840
GAAAAATCGGAAGAACATGAATTGGCATCTGTCCCCACATATAAATTATTACTTTAAATT
rgLysIleGlyArgThr 850         860         870         880         890         900
ATATGATATGCAGGCATGTAGCATGTAGCATATAAATGTTTATATTGTTTTATATATTATAA 910         920         930         940
GTGACCCTTTATTTATTAAACTTCAGCAACCCTTACGATATAAGCTT
```

FIG. 11C

POLYPEPTIDE AND PRODUCTION THEREOF

BACKGROUND OF THE INVENTION

The present invention relates to a novel polypeptide, a DNA sequence coding for the same and a use thereof.

Many cell growth factors have been isolated and their structures have been elucidated since the discovery of epidermal growth factor (hereinafter referred to as EGF) and nerve growth factor (hereinafter referred to as NGF).

Cell growth factors are useful for the elucidation of the mechanism of cell differentiation and cell multiplication mechanism, and some of them, including human EGF, are expected to be useful as drugs. Accordingly, studies thereon have become increasingly prevalent in recent years.

Although the human NGF gene have been isolated, there has been no reports concerning the production of human NGF in large amounts by use of recombinant DNA techniques.

If a novel polypeptide promoting the growth of animal cells is obtained, new investigations can be made thereby. Such novel polypeptides having activities similar to known growth factors may also be utilized as drugs.

For the purpose of discovering such a novel peptide, the present inventors used a DNA sequence encoding NGF as a probe and cloned a DNA sequence hybridizable therewith from cDNA libraries of a human glibma. As a result, the inventors succeeded in obtaining a DNA (cDNA) sequence coding for a novel polypeptide. The cDNA of the present invention may be expressed in a host cell to produce the novel polypeptide. This polypeptide may further be used as a reagent for studies relating to the differentiation, growth and survival of animal cells. The polypeptide may further be used as a drug. The present inventors have made further investigations, based on the information described above, and consequently completed this invention.

SUMMARY OF THE INVENTION

It is therefore an object of the present invention to provide a novel polypeptide useful as a reagent for research investigations or as a drug. Other objects will be apparent from the following description and appended drawings.

The present invention provides:

(1) a polypeptide (I) including the following amino acid sequence (II) in a molecule thereof:

```
TyrAlaGluHisLysSerHisArgGlyGluTyrSerValCys     (II)
AspSerGluSerLeuTrpValThrAspLysSerSerAlaIle
AspIleArgGlyHisGlnValThrValLeuGlyGluIleLys
ThrGlyAsnSerProValLysGlnTyrPheTyrGluThrArg
CysLysGluAlaArgProValLysAsnGlyCysArgGlyIle
AspAspLysHisTrpAsnSerGlnCysLysThrSerGlnThr
TyrValArgAlaLeuThrSerGluAsnAsnLysLeuValGly
TrpArgTrpIleArgIleAspThrSerCysValCysAlaLeu
SerArgLysIleGlyArg
```

(this amino acid sequence is hereinafter also referred to as formula [II] for brevity), (2) a DNA coding for the polypeptide described in (1), (3) a vector including the DNA sequence described in (2), (4) a transformant transformed by the vector described in (3), and (5) a process for producing the polypeptide (I) which comprises cultivating the transformant described in (4) in a culture medium to produce and accumulate the polypeptide described in (1) in a culture.

BRIEF DESCRIPTION OF THE DRAWINGS

FIG. 3 shows a comparison of the amino acid sequence (the upper row) of the polypeptide (I) of the present invention obtained in Example 1 with an amino acid sequence (the lower row) of human βNGF;

FIG. 5 shows a nucleotide sequence of the DNA including the polypeptide (I) cDNA in the plasmid pHNT2 obtained in Example 2, and an amino acid sequence translated therefrom;

FIG. 11 shows a nucleotide sequence of a rat polypeptide (I) gene obtained in Example 13, and an amino acid sequence translated therefrom.

DESCRIPTION OF THE PREFERRED EMBODIMENT

Figure 1:
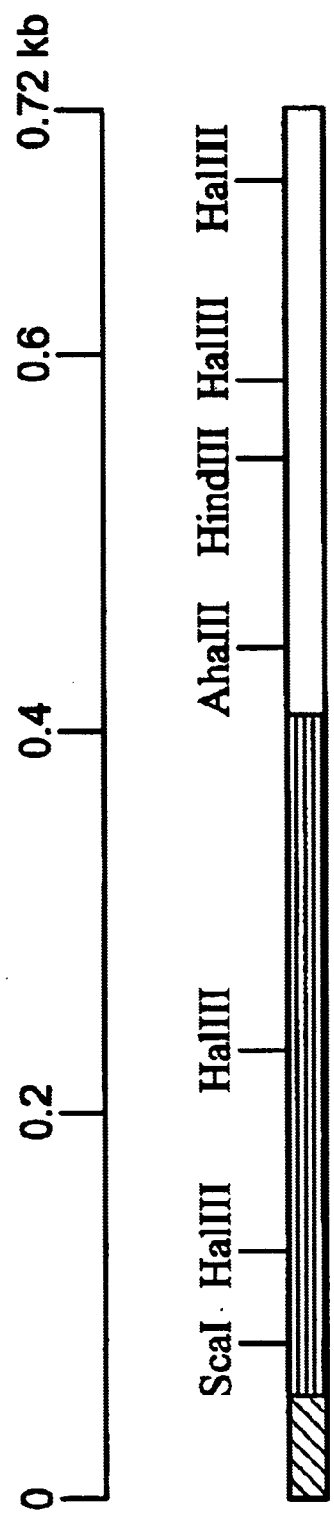
FIG. 1 is a restriction enzyme map of a DNA including a polypeptide (I) cDNA in plasmid pUNK5 obtained in Example 1.

The polypeptide (I) of the present invention includes a polypeptide having the amino acid sequence of formula [II] and a polypeptide further having a threonine residue added to the C-terminus of the amino acid sequence of formula [II]. Further, the polypeptide (I) of the present invention includes a polypeptide having several amino acid residues added to the N-terminus and/or the C-terminus of the amino acid sequence of formula [II]. In addition to the polypeptides described above, the polypeptide (I) of the present invention includes portions of the above polypeptides which have the same activity as the above polypeptides, and polypeptides in which portions of the above amino acid sequences are replaced with one or more different amino acids or amino acid sequences, or in which one or more different amino acids or amino acid sequences are added to or inserted into the above amino acid sequences, and which have the same activity as the above polypeptides.

The polypeptide (I) having the following amino acid sequence (II') in which Thr is added to the C-terminus of the amino acid sequence (II) was produced by *E. coli* transformants in Examples mentioned below.

TyrAlaGluHisLysSerHisArgGlyGluTyrSerValCys    (II')

AspSerGluSerLeuTrpValThrAspLysSerSerAlaIle

AspIleArgGlyHisGlnValThrValLeuGlyGluIleLys

ThrGlyAsnSerProValLysGlntyrPheTyrGluThrArg

CysLysGluAlaArgProVallysAsnGlyCysArgGlyIle

AspAspLysHisTrpAsnSerGlnCysLysThrSerGlnThr

TyrValArgAlaLeuThrSerGluAsnAsnLysLeuValGly

TrpArgTrpIleArgIleAspThrSerCysValCysAlaLeu

SerArgLysIleGlyArgThr

The polypeptide (I) having the amino acid sequence (II) or (II') may also be expressed using animal cell transformants.

When the polypeptide (I) is produced by using recombinant DNA techniques, a methionine residue corresponding to initiation codon ATG upstream from a gene coding for the polypeptide (I) may be added to the N-terminus of the polypeptide (I).

The DNA coding for the polypeptide (I) of the present invention can be obtained, for example, by the following process:

(1) Messenger RNA (mRNA) is isolated from polypeptide (I)-producing cells.

(2) Single stranded complementary DNA (cDNA) is synthesized from the mRNA, followed by synthesis of double stranded DNA.

(3) The complementary DNA is introduced into a plasmid or a phage.

(4) A host cell is transformed with the recombinant phage or plasmid thus obtained.

(5) After culturing of the transformants thus obtained, the plasmid or the phage containing the desired DNA is isolated from the transformants by an appropriate method such as plaque hybridization or colony hybridization.

(6) The desired cloned DNA sequence is cut out from the plasmid or the phage.

(7) The cloned DNA is subcloned into an appropriate plasmid.

The mRNA coding for the polypeptide (I) can be obtained by polypeptide (I)-producing cells, for example, cells, tissues and organs of animals such as human and rat, specifically by human gliomas, human glial cells, human placenta, rat gliomas, kidneys, livers, hearts, brains, spleens, thymuses, lungs and submandibular glands.

Suitable methods for preparing the mRNA from the polypeptide (I)-producing cells include the guanidine thiocyanate method [J. M. Chirgwin et al., *Biochemistry* 18, 5294 (1979)] and the like.

Using the mRNA thus obtained as a template, cDNA is synthesized by use of reverse transcriptase, for example, in accordance with the method of H. Okayama et al. [*Molecular and Cellular Biology* 2, 161 (1979); *ibid.* 3, 280 (1983)] or the method of U. Gubler and B. J. Hoffman [*Gene* 25, 263 (1983)]. The cDNA thus obtained is introduced in the plasmid to produce human cDNA libraries.

The plasmids into which the cDNA may be introduced include, for example, pBR322 [*Gene* 2, 95 (1977)], pBR325 [*Gene* 4, 121 (1978)], pUC12 [*Gene* 19, 259 (1982)], pUC13 [*Gene* 19, 259 (1982)], pUC18 [*Gene* 33, 103 (1985)], pUC19 [*Gene* 33, 103 (1985)], pUC118 [*Methods in Enzymology* 153, 3 (1987)], pUC119 [*Methods in Enzymology* 153, (1987)]. However, any other plasmid can be used as long as it is replicable and sustainable in the host cell. The phage vectors into which the cDNA may be introduced include, for example, λgt11 [R. Young and R. Davis, *Proc. Natl. Acad. Sci. U.S.A.* 80, 1194 (1983)]. However, any other phage vector is suitable, if growable in the host cell.

The methods for inserting the cDNA into the plasmid include, for example, the method described in T. Maniatis et al., *Molecular Cloning, A Laboratory Manual*, Cold Spring Harbor Laboratory, p.239 (1982). The methods for inserting the cDNA into the phage vector include, for example, the method of T. V. Hyunh et al. [*DNA Cloning, A Practical Approach* 1, 49 (1985)]. The plasmid or the phage vector thus obtained is introduced in the appropriate cells such as *E. coli*.

Examples of *E. coli* described above include *E. coli* K12DH1 [*Proc. Natl. Acad. Sci. U.S.A.* 60, 160 (1968)], JM103 [*Nucl. Acids Res.* 9, 309 (1981)], JA221 [*Journal of Molecular Biology* 120, 517 (1978)], HB101 [*Journal of Molecular Biology* 41, 459 (1969)] and C600 [*Genetics* 39, 440 (1954)].

Suitable methods of transformation of the host cell with the plasmids include, for example, the calcium chloride method or the calcium chloride/rubidium chloride method described in T. Maniatis et al., *Molecular Cloning*, Cold Spring Harbor Laboratory, p.249 (1982). Further, for example, phage vectors can be transduced into multiplied *E. coli*. using the in vitro packaging method.

The cDNA libraries containing the polypeptide (I) cDNA can be obtained by the above-mentioned methods. However, they are also available as commercial products. For example, a human glioma-derived cDNA library and a human placenta- derived cDNA library are available from Clontech Laboratories, Inc., U.S.A. Examples of suitable methods for cloning polypeptide (I) cDNA from the cDNA library include the plaque hybridization method using a labeled probe or the colony hybridization method [T. Maniatis et al., *Molecular Cloning, A Laboratory Manual*, Cold Spring Harbor Laboratory (1982)]. Any DNA can be employed as a DNA used as the probe in the above hybridization as long as it is hybridizable with the DNAs coding for the polypeptide (I). Such DNA include, for example, cDNA coding for all or part of NGF, genomic DNA, chemically synthesized DNA, and oligonucleotides chemically synthesized on the basis of the amino acid sequence of NGF. Examples of the above-mentioned NGFs include mouse NGF [*Proc. Natl. Acad. Sci. U.S.A.* 68, 2417 (1971), *Nature* 302, 538 (1983)], human NGF [*Nature* 303, 821 (1983)] and NGFs of other animals.

The polypeptide (I) cDNA thus cloned may be subcloned into, for example, pBR322, pUC12, pUC13, pUC18, pUC19, pUC118 and pUC119 to express the polypeptide (I) cDNA, if necessary.

The nucleotide sequence of the DNA thus obtained is determined by, for example, the Maxam-Gilbert method [A. M. Maxam and W Gilbert, *Proc. Natl. Acad. Sci. U.S.A.* 74, 560 (1977)] or the dideoxy method [J. Messing et al., *Nucleic Acids Research* 9, 309 (1981)] to confirm the existence of the polypeptide (I) cDNA. As a result, if the whole region coding for the polypeptide (I) is not covered, the cDNA may be cloned again by plaque hybridization using that DNA fragment as the probe or colony hybridization to obtain any region not covered.

As described above, the DNA coding for the polypeptide (I) can be obtained.

In addition to the above methods, the DNA including the DNA segment coding for the polypeptide (I) of the present invention can also be obtained by cloning from genomic DNA libraries of human, rat, mouse and the like. Further, the DNA coding for the polypeptide (I) may be obtained by chemical synthesis based on the amino acid sequence of the polypeptide (I) elucidated from the nucleotide sequence of the DNA from the nucleotide sequence of the DNA thus cloned.

Any DNA may be used as the DNA coding for the polypeptide (I) of the present invention as long as it codes for the polypeptide (I). Illustrative examples include a DNA represented by the nucleotide sequence of the following formula [III] and a DNA in which ACA is further added to the 3'-terminus of the nucleotide sequence of the following formula [III]:

```
TACGCGGAGC ATAAGAGTCA CCGAGGGGAG TACTCGGTAT    (III)

GTGACAGTGA GAGTCTGTGG GTGACCGACA AGTCATCGGC

CATCGACATT CGGGGACACC AGGTCACGGT GCTGGGGGAG

ATCAAAACGG GCAACTCTCC CGTCAAACAA TATTTTTATG

AAACGCGATG TAAGGAAGCC AGGCCGGTCA AAAACGGTTG

CAGGGGTATT GATGATAAAC ACTGGAACTC TCAGTGCAAA

ACATCCCAAA CCTACGTCCG AGCACTGACT TCAGAGAACA

ATAAACTCGT GGGCTGGCGG TGGATACGGA TAGACACGTC

CTGTGTGTGT GCCTTGTCGA GAAAAATCGG AAGA
```

(this nucleotide sequence is hereinafter also referred to as formula [III] for brevity).

In some cases, portions of the nucleotide sequence constituting this DNA may be removed or replaced. Further, one or more additional bases may be added to or inserted into this DNA. It is preferable that the removal, replacement or addition of bases is carried out by a codon unit corresponding to the expression of the corresponding amino acid or acids.

The DNA coding for the polypeptide (I) thus obtained can be used as it is, or cut out with a restriction enzyme if desired, depending upon the intended use.

Suitable methods for obtaining the polypeptide (I) of the present invention include (1) isolating the polypeptide (I) from the organisms of animals including human, (2) preparing the polypeptide (I) by peptide synthesis and (3) producing the polypeptide (I) by using gene recombination. The third method is industrially preferable.

Examples of expression systems (host-vector systems) for producing the polypeptide (I) using recombinant DNA techniques include expression systems of bacteria, actinomycetes, yeast, molds, insect cells and animal cells.

Suitable expression methods include (a) producing and accumulating gene products in cells, (b) secreting gene products out of cells and accumulating them in culture media, and (c) secreting gene products into periplasms.

In order to secrete the polypeptide (I) in the above methods of (b) and (c), a DNA coding for a signal peptide or a DNA coding for a signal peptide and a propeptide (prepro) may be ligated to the 5'-terminus of the DNA coding for the polypeptide (I). Any peptide can be used as the above-mentioned signal peptide as long as it can induce secretion of the polypeptide (I). Examples of such signal peptides include the signal peptides of *E. coli* enterotoxin and mutants thereof, signal peptides of *Bacillus amyloliquefaciens* neutral protease and α-amylase, signal peptides of *Bacillus brevis* middle wall proteins, signal peptides of *Saccharomyces cerevisiae* invertase, phosphatase, α-factor and killer factor, a signal peptide of *Aspergillus awamori* glucoamylase, a signal peptide of the polypeptide (I), a signal peptide of egg-white lysozyme and its mutants thereof, a signal peptide of human interleukin-2, and signal peptides of human, mouse, rat, chicken and bovine NGFs. Examples of suitable propeptides include propeptides of *S. cerevisiae* α-factor and killer factor, a propeptide of *A. awamori* glucoamylase, a propeptide of the polypeptide (I), and propeptides of human endothelin, human, mouse, rat, chicken and bovine NGFs.

In addition to the above methods, the polypeptide (I) can also be obtained by producing a fused protein of the polypeptide (I) and another protein and then cleaving it with an appropriate protease.

An initiation codon may be added to the 5'-terminus of the above DNA containing the DNA segment coding for the polypeptide (I) such as the DNA coding for the polypeptide (I), the DNA coding for the signal peptide and the polypeptide (I), or the DNA coding for the signal peptide, the propeptide and the polypeptide (I), and a termination codon may be added downstream therefrom. The resulting DNA may be inserted downstream from a promoter in a vector, thereby constructing a polypeptide (I) expression vector.

As the vector used for expression of the polypeptide (I), any vector can be used as long as it functions in the host cells chosen. Examples of *E. coli* expression vectors include pBR322, pBR325, pUC12 and pUC13, pUC18, pUC19, pUC118, pUC119 and derivatives thereof. Examples of *Bacillus subtilis* expression vectors include pUB110, pC194, pE194, pTB5 and derivatives thereof, and examples of *B. brevis* expression vectors include pUB110, pHY481, pC194, pHY500, pNU200 and derivatives thereof. Examples of *S. cerevisiae* expression vectors include pSH19, pSH15 and derivatives thereof, and examples of *Schizosaccharomyces pombe* expression vectors include pDB248, pPA-4 and derivatives thereof. Examples of animal cell expression vectors include retrovirus vectors, vaccinia virus vectors, bovine papilloma virus vectors and SV40-series vectors (such as pKSV-10, pSV2-dhfr and pTB389).

Any promoter is suitable as long as it functions in the host cells chosen.

For example, when *E. coli* vectors are used, suitable promoters include the trp promoter, the lac promoter, the tac promoter, the λPL promoter, the recA promoter and the T7 promoter. When *B. subtilis* vectors are used, examples of suitable promoters include the SPO1 promoter, the P1 promoter and the neutral protease gene promoter. When *B. brevis* vectors are used, examples of suitable promoters include the extracellular major protein gene promoter and the SPO1 promoter. When *S. cerevisiae* vectors are used, examples of suitable promoters include the GLD promoter, the PHO5 promoter, the GAL10 promoter, the GAL1 promoter, the PGK promoter and the α-factor promoter. When *S. pombe* vectors are used, examples of suitable promoters include the GLD promoter and an SV40 promoter. When animal cell vectors are used, examples of suitable promoters include an SV40 promoter, the LTR promoter and the metallothionein promoter.

In order to increase the expression efficiency, it is preferable in yeast to use a terminater (such as a PGK terminater) downstream from the DNA coding for the polypeptide (I), and it is preferable in an animal cell to use an enhancer, an RNA splicing signal, a poly A addition signal or a selected marker.

Methods for constructing the expression vector of the present invention are known per se and described, for example, in *Molecular Cloning, A Laboratory Manual*, Cold Spring Harbor Laboratory (1982).

Using the polypeptide (I) expression vector thus prepared, the host cell may be transformed.

Suitable host cells include bacteria such as *E. coli, B. subtilis* and *B. brevis*, actinomycetes such as *Streptomyces lividans*, yeast such as *S. cerevisiae, Schizosaccharomyces pombe* and *Pichia pastoris*, molds such as *Aspergillus orizae, Aspergillus nidulans* and *Aspergillus niger*, and animal cells such as monkey cell COS-7 cell, Vero cell, Chinese hamster ovary cell (CHO) and mouse L cell.

More particularly, suitable *E. coli* strains include DH1, JM103, JA221, HB101, C600, MV1184 and mutants thereof. Suitable *B. subtilis* strains include MI114, 1A274 and mutants thereof. Suitable *B. brevis* strains include 47, 47-5, HPD31 and mutants thereof. Suitable *S. cerevisiae* strains include AH22R$^-$, NA47-3A$\rho^-$, TB39$\rho^-$ and mutants thereof. Suitable *S. pombe* strains include ATCC38399, TH168 and mutants thereof.

Methods for the transformation of host cells using the DNA sequence of the present invention such as the polypeptide (I) expression plasmid, are known in the art. *E. coli* may be transformed, for example, by the method of Cohen et al. [*Proc. Natl. Acad. Sci. U.S.A.* 69, 2110 (1972)]. *B. subtilis* may be transformed, for example, by the protoplast method [*Molecular & General Genetics* 168, 111 (1979)] or the competent method [*J. Mol. Biol.* 56, 209 (1971)). *B. brevis* may be transformed, for example, by the method of Takahashi et al. [*J. Bacteriol.* 156, 1130 (1983)]. *S. cerevisiae* and *S. pombe* may be transformed, for example, by the method of Hinnen [*Proc. Natl. Acad. Sci. U.S.A.* 75, 1929 (1978)] or the lithium method [*J. Bacteriol.* 153, 163 (1983)]. Animal cells may be transformed, for example, by the method of Graham [*Virology* 52, 456 (1973)].

As described above, the transformants transformed with the DNA containing the DNA segment coding for the polypeptide (i) may be obtained in accordance with the present invention.

When transformants wherein the host cells are bacteria, actinomycetes, yeast or mold are cultivated, a liquid medium is suitable as a medium used for culture. Carbon sources, nitrogen sources, inorganic compounds and other nutrients necessary for growth of the transformant are contained therein. Suitable carbon sources include, for example, glucose, dextrin, soluble starch and sucrose. Suitable nitrogen sources include inorganic or organic materials such as ammonium salts, nitrates, amino acids, corn steep liquor, peptone, casein, meat extracts, soybean meal and potato extract solution. Suitable inorganic compounds include, for example, calcium chloride, sodium dihydrogenphosphate and magnesium chloride.

The pH of the medium is preferably about 5 to 8.

When the host is *E. coli*, it is preferable that the medium used for cultivation is, for example, M9 medium containing glucose and Casamino Acids [Miller, *Journal of Experiments in Molecular Genetics*, 431–433, Cold Spring Harbor Laboratory, New York, (1972)]. The cultivation is usually carried out at 14 to 43° C. for about 3 to 24 hours, with aeration or shaking if necessary.

When the host is Bacillus, the cultivation is usually carried out at about 30 to 40° C. for about 16 to 96 hours, with aeration or agitation if necessary.

When yeast transformants are cultivated, examples of suitable media include Burkholder minimum medium [K. L. Bostian et al., *Proc. Natl. Acad. Sci. U.S.A.*, 77, 4505 (1980)]. The pH of the medium is preferably adjusted to about 5 to 8. The cultivation is usually carried out at about 20 to 35° C. for about 24 to 144 hours, with aeration or shaking if necessary.

When the animal cell transformants are cultivated, examples of suitable media include MEM medium containing about 5 to 20% fetal calf serum [*Science* 122, 501 (1952)], DMEM medium [*Virology* 8, 396 (1959)], RPMI1640 medium [*J. Am. Med. Assoc.* 199, 519 (1967)] and 199 medium [*Proc. Soc. Exp. Biol. Med.* 73, 1 (1950)]. The pH is preferably about 6 to 8. The cultivation is usually carried out at about 30 to 40° C. for about 15 to 60 hours, with aeration or shaking if necessary.

The polypeptide (I) of the present invention may be produced and accumulated inside or outside the cells.

When intracellular polypeptide (I) is extracted from the cultivated cells, the cells are collected after cultivation by methods known in the art. Then, the collected cells are suspended in an appropriate buffer solution containing a protein denaturant such as urea or guanidine hydrochloride, or a surface-active agent such as Triton X-100, followed by centrifugation to obtain a supernatant containing the polypeptide (I). Alternatively the collected cells may be disrupted by ultrasonic treatment, treatment with an enzyme such as lysozyme or freeze-thawing, followed by centrifugation to obtain a supernatant containing the polypeptide (I).

The purification of the polypeptide (I) contained in the culture supernatant or produced and accumulated in the cells can be performed by an appropriate combination of known purification methods. These known purification methods include methods utilizing a difference in solubility such as salt precipitation and solvent precipitation; methods mainly utilizing a difference in molecular weight such as dialysis, ultrafiltration, gel permeation chromatography and SDS-polyacrylamide gel electrophoresis; methods utilizing a difference in electric charge such as ion-exchange column chromatography; methods utilizing specific affinity such as affinity chromatography; methods utilizing a difference in hydrophobicity such as reverse-phase high performance liquid chromatography; and methods utilizing a difference in isoelectric point such as isoelectro focusing electrophoresis.

If the polypeptide (I) thus obtained has activity, it may be used as it is. If it does not exhibit activity, it may be used after activation by an enzymatic or nonenzymatic method.

The activity of the polypeptide (I) of the present invention can be determined by enzyme immunoassays, radio immunoassays or the like.

The polypeptide (I) has the functions of promoting the differentiation and growth of animal cells, promoting the survival of animal cells, enhancing gene expression, and inducing the production of proteins and enzymes. Hence, the activity of the polypeptide (I) can be assayed, taking these functions as indices. Because of its homology to NGF, polypeptide (I) may have activities and functions similar to those of NGF. Illustrative examples of such activities and functions include the promoting neurite outgrowth in PC12 cells [L. A. Greene, *Brain Research* 133, 350 (1977); R. Heumann et al., *Experimental Cell Research* 145, 179

(1983)] and the promoting function of the survival of chicken embryo sensory ganglia (dorsal root ganglio) [A. M. Davies & R. M. Lindsay, *Developmental Biology* 111, 62 (1985)].

The polypeptide (I) of the present invention is useful as a reagent for studies relating to the differentiation, growth and survival of animal cells. When the polypeptide (I) is used for these studies, for example, it is preferable to add the polypeptide (I) to a culture medium for animal cells to give a final concentration of about 0.1 to 1,000 ng/ml, more preferably about 1 to 100 ng/ml. The animal cells may be cultivated in the culture medium containing the polypeptide (I), and thereby the degree of the differentiation, growth and survival of the animal cells can be determined.

Polypeptide (I) may also function in the repair of damaged tissues and organs, and therefore the polypeptide (I) may be useful as a drug.

Furthermore, the DNA coding for the polypeptide (I) can be utilized as a probe for detection and determination of polypeptide (I) mRNA and for cloning of NGF genes.

When the DNA encoding the polypeptide (I) is used as a probe, for example, 0.5 μg of the DNA (about 300 bp) coding for the polypeptide (I) is labeled with [α-$^{32}$P]dCTP (>400 Ci/mmol) (Amersham, UK) by using a nick translation kit supplied by Amersham (about $10^7$ cpm). In cloning by plaque hybridization, the hybridization is performed using 0.005 μg ($10^5$ cpm) of the above labeled probe per filter.

When bases, amino acids and so on are indicated by the abbreviations in this specification and drawings, the abbreviations adopted by IUPAC-IUB Commission on Biochemical Nomenclature or commonly used in the art are employed. For example, the following abbreviations are used. When the optical isomers are capable of existing with respect to the amino acid, the L-form is represented unless otherwise specified.

| | |
|---|---|
| DNA | Deoxyribonucleic acid |
| A | Adenine |
| C | Cytosine |
| G | Guanine |
| T | Thymine |
| Ala | Alanine |
| Arg | Arginine |
| Asn | Asparagine |
| Asp | Aspartic acid |
| Cys | Cysteine |
| Gln | Glutamine |
| Glu | Glutamic acid |
| Gly | Glycine |
| His | Histidine |
| Ile | Isoleucine |
| Leu | Leucine |
| Lys | Lysine |
| Met | Methionine |
| Phe | Phenylalanine |
| Pro | Proline |
| Ser | Serine |
| Thr | Threonine |
| Trp | Tryptophan |
| Tyr | Tyrosine |
| Val | Valine |
| Boc | t-Butyloxycarbonyl |
| MeBzl | p-Methylbenzyl |
| Bzl | Benzyl |
| -P | Polystyrene resin for solid synthesis of peptide |
| PAM | p-Oxymethylphenylacetainidomethyl resin |
| AcOH | Acetic acid |
| OBzl | Benzyl ester |
| Tos | Tosyl |
| Br-z | 2-Bromobenzyloxycarbonyl |
| Cl-z | 2-Chlorobenzyloxycarbonyl |

The microorganisms obtained in Reference Example 1 described below and the transformants obtained in Examples described below were deposited at the Institute for Fermentation, Osaka, Japan (IFO), and further at Fermentation Research Institute, Agency of Industrial Science and Technology, Ministry of International Trade and Industry, Japan (FRI) under the Budapest treaty. Their accession numbers and deposit dates are shown in Table 1.

TABLE 1

| Microorganism | IFO | FRI |
|---|---|---|
| *Escherichia coli* MV1184/pUNK5 (Example 1) | IFO 14832 (Feb. 10, 1989) | FERM BP-2304 (Feb. 22, 1989) |
| *Escherichia coli* BL21(DE3)/ pENGFT102 (Example 4) | IFO 14874 (May 11, 1989) | FERM BP-2420 (May 17, 1989) |
| *Escherichia coli* DH1/PNTL145 (Example 5) | IFO 14873 (May 11, 1989) | FERM BP-2421 (May 17, 1989) |
| *Saccharomyces cerevisiae* TB39p$^-$ (Reference Example 1) | IFO 10467 (Apr. 24, 1989) | FERM BP-2399 (Apr. 25, 1989) |
| *Saccharomyces cerevisiae* TB39p$^-$/pANT341T (Example 9) | IFO 10475 (Jul. 18, 1989) | FERM BP-2530 (Jul. 26, 1989) |
| *Escherichia coli* BL2l(DE3)/pLysS, pENGFT102 (Example 10) | IFO 14903 (Jul. 14, 1989) | FERM BP-2529 (Jul. 26, 1989) |
| '*Escherichia coli* DHl/pRNT18 (Example 13) | IFO 14934 (Sep. 7, 1989) | FERM BP-2618 (Sep. 30, 1989) |
| L-H14-1 (Example 15) | IFO 50223 (Jan. 30, 1990) | FERM BP-2754 (Feb. 7, 1990) |

The present invention will hereinafter be described in detail with the following Reference Examples and Examples. It is understood that these Reference Examples and Examples are not intended to limit the scope of the present invention.

REFERENCE EXAMPLE 1

Preparation of *S. cerevisiae* TB39 ρ$^-$

*S. cerevisiae* NA74-3A (a, pho9, his4, leu2) (IFO 10430, FERM BP-1947) (refer to Japanese Patent Application (Laid-open) No. 63-283716/1988 corresponding to EP-317, 209A) was crossed with *S. cerevisiae* DK-13D (α, leu2, trp1, his3) [*Molecular and Cellular Bioloqy* 4, 771 (1984)]. One of the resulting strains was treated with ethidium bromide to obtain its respiratory-deficient strain *S. cerevisiae* TB39 ρ$^-$(α, MAta, leu2, his3, pho9, ρ$^-$) (IFO 10467, FERM BP-2399).

REFERENCE EXAMPLE 2

Preparation of Anti-N-Terminal Peptide Antibody (1) Synthesis of H-Tyr-Ala-Glu-His-Lys-Ser-His-Arg-Gly-Glu-Tyr-Ser-val-Cys-OH This peptide was synthesized by a solid synthesizing method using an automatic peptide synthesizer Model 430A (Applied Biosystems). As a program, "Standard 1" was used. The synthesis was basically conducted in accordance with the method described in R. B. Merrifield, Adv. Enzymol. 32, 221–296 (1969). Boc-Cys(MeBzl) PAM-P (0.5 mmol/g) was used as a resin, and the synthesis was carried out sequentially from the carboxyl terminus. As Boc-amino acids, there were used Boc-Val, Box-Ser(Bzl), Boc-Tyr(Br-Z), Boc-Glu(OBzl), Boc-Gly, Boc-Arg(Tos), Boc-His(Tos), Boc-Lys(Cl-Z) and Boc-Ala. A peptide resin was synthesized up to the amino terminus Tyr, and then taken out of the synthesizer, followed by drying.

To 1 g of the peptide resin were added 1.5 ml of p-cresol and 0.5 ml of 1, 2-ethandithiol, and about 8 ml of liquid hydrogen fluoride was further added thereto, followed by reaction at 0° C. for 2 hours. After the reaction was completed, hydrogen fluoride was removed under reduced pressure in a desiccator, and washed with a 0.1% solution of 2-mercaptoethanol in diethyl ether, followed by washing with diethyl ether to remove most of the included reagents. The peptide was extracted with 10 ml of 3% acetic acid, and the resin included in the extracted solution was removed by filtration. The filtrate was purified by gel permeation chromatography using a Sephadex G-25 column. The conditions of the gel permeation chromatography were as follows:

Column size: 2.8×60 cm; Detecting wavelength: 280 nm;
Solvent: 3% acetic acid; Flow rate: 40 ml/hr Fractions containing the peptide were collected and lyophilized to obtain a powdery sample. The resulting powdery sample was further purified by reverse-phase high performance liquid chromatography under the following conditions:

Column: YMC pack, A-324 ODS 10×250 mm;
Column temperature: 25° C.;
Eluent A: 0.1% trifluoroacetic acid-99.9% distilled water;
Eluent B: 0.1% trifluoroacetic acid-99.9% acetonitrile;
Elution program: 0 minute (90% A+10% B), 30 minutes (60% A+40% B);
Elution rate: 2 ml/minute;
Detecting wavelength: 230 nm Main peak fractions eluted at a retention time of 23.0 minutes under these conditions were collected, and passed through a Bio RAD AG1×8 column (AcOH type, 1.8×5 cm). Washings were also collected. Then, acetonitrile was removed by distillation, followed by lyophilization. Thus, 56 mg of white powder was obtained. The resulting product showed a sharp single peak at 23.0 minutes under the same conditions as with the above-mentioned high performance liquid chromatography Determination of free SH groups by the method described in G. L. Elman, Arch. Biochem. Biophys. 82, 70–77 (1959): 114%

Values of analysis of amino acids: Ser 1.65(2); Glu 2.13(2); Gly 1.00(1); Ala 1.04(1); 1/2Cys 0.82(1); Val 1.03(1); Tyr 1.97(2); Lys 0.95(1); His 1.72(2); Arg 1.00(1) Recovery: 74%

1/2Cys was determined by the performic oxidation method. The values in parentheses show theoretical values.

(2) Preparation of Conjugate of N-terminal Peptide and Hemocyanin

In 4 ml of 0.2 M phosphate buffer (pH 7.3) were dissolved 5 mg of the N-terminal peptide obtained in (1) described above and 10 mg of hemocyanin, and 400 µl of 2.5% glutaraldehyde cooled in ice water was added thereto drop by drop while stirring. After stirring under ice cooling for 3 hours, the dialysis against distilled water was carried out to obtain a conjugate of the N-terminal peptide and hemocyanin.

(3) Preparation of Conjugate of N-terminal Peptide and Bovine Serum Albumin

To 3 ml of 0.1 M phosphate buffer (pH 7.5) was added 132 mg of bovine serum albumin (BSA) (solution A). To 200 µl of dimethylformamide was added 11.2 mg of N-(γ-maleimidebutyloxy)succinimide (GMBS) (solution B). The solution B was added dropwise to the solution A while stirring with a stirrer, and the mixture solution was reacted at 30° C. for 30 minutes. Then, the reaction product was purified by a Sephadex G-25 column (1.5×20 cm) using 0.1 M phosphate buffer (pH 6.5)-0.1 M NaCl as an eluent to obtain bovine serum albumin in which maleimide groups were introduced.

In 0.1 M phosphate buffer-5 mM EDTA was dissolved 5 mg of the peptide obtained in (1) described above, and 20 mg of the maleimide group-introduced bovine serum albumin was added thereto (the total volume is not more than 5 ml), followed by reaction at 30° C. for 60 minutes. Then, PBS (phosphate-buffered saline) was added thereto until the total volume is 12 ml, and thereby a conjugate of the N-terminal peptide and bovine serum albumin was obtained.

(4) Preparation of Anti-Polypeptide (I) N-Terminal Peptide

The conjugate of the N-terminal peptide and hemocyanin obtained in (2) described above was thoroughly mixed with Freund's complete adjuvant, and the resulting mixture was subcutaneously injected into the rabbits. Thereafter, at 2-week intervals, the conjugate of the N-terminal peptide and bovine serum albumin obtained in (3) described above was mixed with Freund's incomplete adjuvant, and the resultant mixture was injected into the same rabbits.

Blood collected from the rabbits immunized as described above was centrifuged to obtain an anti-polypeptide (I) N-terminal peptide antibody.

EXAMPLE 1

Cloning of Polypeptide (I) cDNA

*Escherichia coli* Y1090 was infected with the human glioma-derived λgt11 cDNA libraries (Clontech Laboratories, Inc.), and then about $6 \times 10^5$ phage were spread on an agar plate containing NZCYM medium described in *Molecular Cloning, A Laboratory Manual*, Cold Spring Harbor Laboratory (1982), followed by cultivation at 37° C. for 5 hours. Then, a nylon membrane was placed on the plate, and removed after it was allowed to stand for 1 minute. This nylon membrane was soaked in 0.5 M NaOH-1.5 M NaCl, then in 1.5 M NaCl-0.5 M Tris-HCl (pH 8.0), and further in 2×SSC [Refer to *Molecular Cloning, A laboratory Mannual*, Cold Spring Harbor Laboratory (1982)]. After air drying, the membrane was allowed to stand at 80° C. for 2 hours.

A DNA (about 0.38 kb) coding for human βNGF [*Nature* 303, 821 (1983)] was chemically synthesized and labeled with [α-$^{32}$P]dCTP by nick translation, thereby preparing a probe.

Using the nylon membrane and the probe obtained in the above, hybridization was carried out according to the method described in *Molecular Cloning, A Laboratory Manual*, Cold Spring Harbor Laboratory (1982). Namely, the nylon membrane was soaked in a hybridization solution containing the probe, and maintained at 65° C. for 16 hours. The nylon membrane was washed with 2×SSC-0.1% SDS at room temperature, and then with 1×SSC-0.1% SDS at 60° C. Thereafter, positive clones were detected by autoradiography.

A cDNA portion was cut out with EcoRI from the clone βGN1321 thus obtained and inserted into the EcoRI site of plasmid pUC118 (Takara Shuzo) to obtain plasmid pUNK5. Using the plasmid pUNK5 thus obtained, *E. coli* MV1184 (Takara Shuzo) was transformed by the method of Cohen et al. (previously described) to obtain transformant *E. coli* MV1184/pUNK5 (IFO 14832, FERM BP-2304).

FIG. 1 shows the restriction enzyme map of the cDNA portion including the polypeptide (I) cDNA contained in the plasmid pUNK5 and having a whole length of about 0.78 kb. In FIG. 1, ☐ shows an untranslated region, ▨ shows a propeptide code region, and ▦ shows a region coding for a polypeptide further having a threonine residue at the C-terminus of the amino acid sequence of formula [II].

Figures 2, 2A:
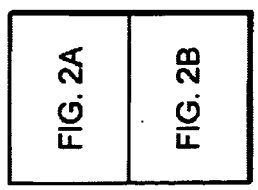
FIG. 2 shows a nucleotide sequence of the DNA including the polypeptide (I) cDNA in the plasmid pUNK5 obtained in Example 1, and an amino acid sequence translated therefrom.

The nucleotide sequence of the cDNA portion obtained in the above was determined by the dideoxy method [Messing et al., *Nucl. Acid. Res.* 9, 309 (1981)]. FIG. 2 shows the determined nucleotide sequence and the amino acid sequence translated thereby. In FIG. 2, the region extending from position −1 to the N-terminus of the amino acid sequence is a portion of the propeptide, and the region of positions 1 to 118 or positions 1 to 119 shows the polypeptide having the amino acid sequence of formula [II] and the polypeptide further having a threonine residue at the C-terminus of the amino acid sequence of formula [II].

FIG. 3 shows the amino acid sequence of the polypeptide (I) determined by the above method, in comparison with the amino acid sequence of the human βNGF described in Ullrich et al., *Nature* 303, 821 (1983). In FIG. 3, the upper row indicates the sequence of 119 amino acids of the polypeptide (I), and the lower row indicates the amino acid sequence of the human βNGF. The same amino acid residue portions are boxed. In the figure, "—" only shows a chemical bond.

As apparent from this comparison, the sequence of 119 amino acids of the polypeptide (I) of the present invention has a homology of about 60% with the amino acid sequence of the above human βNGF.

Further, when the sequence of 119 amino acids of the polypeptide (I) determined as described above is compared with the amino acid sequence of the mouse βNGF shown in Angeletti et al., *Proceedings of National Academy of Sciences, U.S.A.* 68, 2417 (1971) and Scott et al., *Nature* 302, 538 (1983), it has a homology of about 60%.

From the above comparison, the polypeptide (I) of the present invention is considered to be a novel polypeptide.

EXAMPLE 2

Recloning of Polypeptide (I) cDNA

Figure 4:
FIG. 4 is a restriction enzyme map of a DNA including a polypeptide (I) cDNA in plasmid pHNT2 obtained in Example 2.

Using the EcoRI-AhaIII fragment containing the 5'-terminal side of the polypeptide (I) cDNA portion contained in the pUNK5 obtained in Example 1 as a probe, one of the human glioma-derived cDNA libraries (Clontech Laboratories, Inc.) was cloned in a manner similar to that of Example 1. A cDNA portion was cut out with EcoRI from one of many positive clones, λHNT31, thus obtained, and inserted into the EcoRI site of plasmid pUC119 (Takara Shuzo) to obtain plasmid pHNT2. FIG. 4 shows the restriction enzyme map of a polypeptide (I) cDNA (about 1.1 kb) inserted into the plasmid pHNT2. In FIG. 4, ▦ shows a signal peptide code region, ▨ shows a propeptide code region, and ▤ shows a region coding for a polypeptide further having a threonine residue at the C-terminus of the amino acid sequence of formula [II].

The nucleotide sequence of the cDNA portion obtained in the above was determined by the dideoxy method (previously described). FIG. 5 shows the determined nucleotide sequence and the amino acid sequence translated thereby. In FIG. 5, "Signal" indicates the signal peptide, "Pro" indicates the propeptide and "Mature" indicates the polypeptide (I) (mature protein).

EXAMPLE 3

Construction of Polypeptide (I) Expression Vector for *Escherichia coli*

The polypeptide (I) cDNA inserted into the plasmid pUNK5 obtained in Example 1 has an ScaI site near the region coding for the 11th tyrosine residue from the N-terminus of polypeptide (I), and an NsiI site downstream from a termination codon of the polypeptide (I) by 50 bases (refer to FIGS. 2, 4 and 5). A 0.3-kb ScaI-NsiI segment was isolated from the plasmid pUNK5, and adapters NGFTE-1 (35mer), NGFTE-2 (33mer), NGFTE-3 (7mer) and NGFTE-4 (15mer) were ligated thereto with T4 DNA ligase, followed by treatment with restriction enzymes NdeI and BamHI. Thus, a 0.3-kb NdeI-BamHI fragment was obtained (refer to FIG. 6).

These adapters are as follows:

NGFTE-1:5' TATGTACGCGGAGCATAAGAGTCAC-CGAGGGGAGT 3' 35mer

NGFTE-2:5' ACTCCCCTCGGTGACTCTTATGCTC-CGCGTACA 3' 33mer

NGFTE-3:5' TGCCAGG 3' 7mer

NGFTE-4:5' GATCCCTGGCATGCA 3' 15mer

The expression vector pET-3C having a T7 promoter [Rosenberg et al., *Gene* 56, 125 (1987)] was similarly cleaved with NdeI and BamHI to isolate a 4.4-kb NdeI-BamHI fragment.

Figure 6:
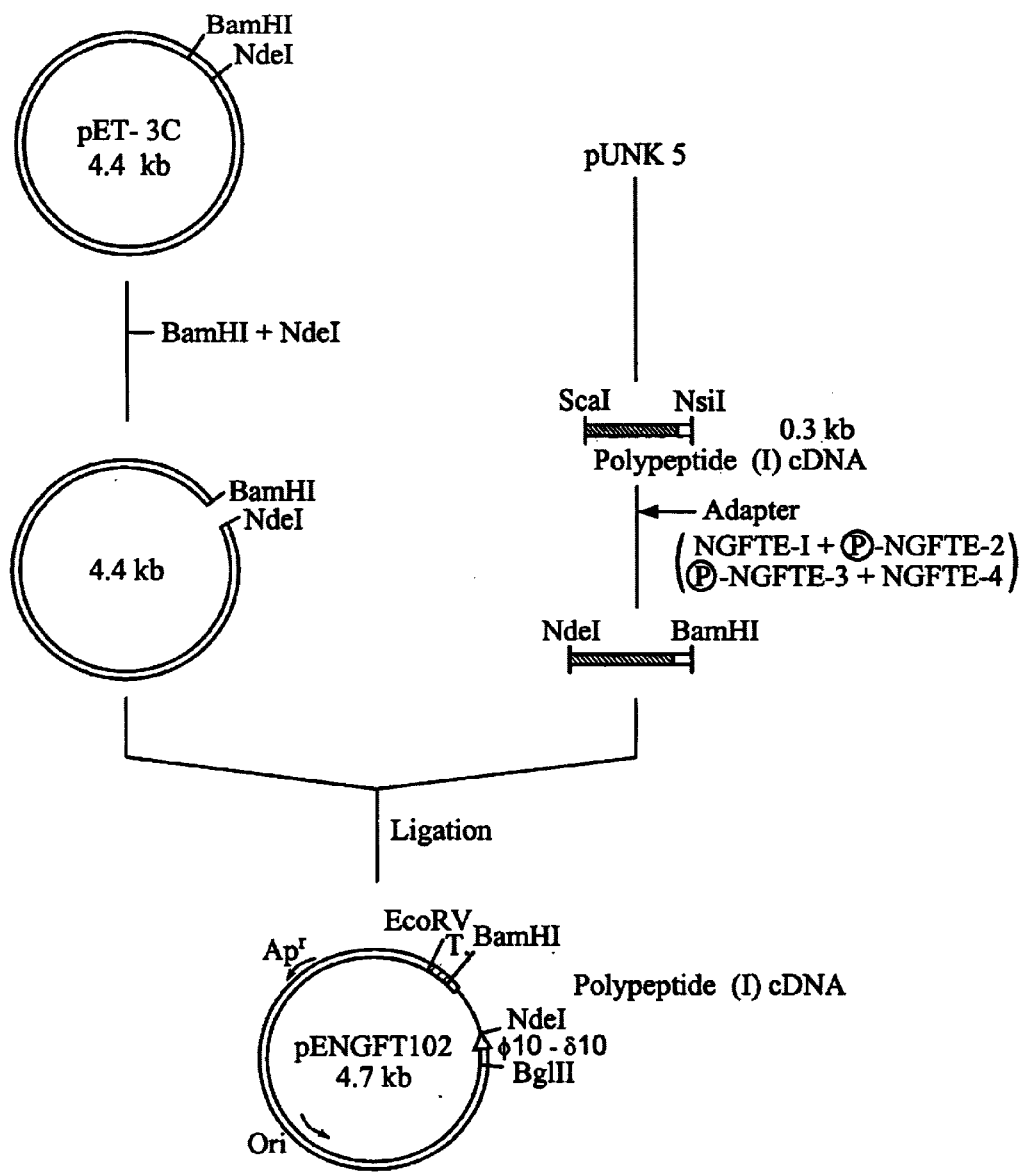
FIG. 6 is a schematic representation showing the construction of the polypeptide (I) expression vector pENGFT102 for *Escherichia coli* obtained in Example 3.

The 4.4-kb NdeI-BamHI fragment obtained above was ligated to the 0.3-kb NdeI-BamHI fragment with T4 DNA ligase, and then the ligated fragment was inserted into *E. coli* DH1 to prepare a transformant. A plasmid isolated from the resulting ampicillin-resistant transformant *E. coli* DH1/pENGFT102 was named pENGFT102 (FIG. 6).

EXAMPLE 4

Isolation of Transformant and Expression

Using the polypeptide (I) expression vector pENGFT102 obtained in Example 3, *E. coli* BL21(DE3) [*Gene* 56, 125 (1987)] was transformed to obtain transformant *E. coli* BL21(DE3)/pENGFT102 (IFO 14874, FERM BP-2420).

The transformant *E. coli* BL21(DE3)/pENGFT102 was cultivated on 5 ml of LB culture medium containing 50 μg/ml ampicillin and 0.2% glucose in a test tube at 37° C. for 16 hours. 1 ml of the resulting culture solution was transferred into a 200-ml flask containing 20 ml of the same medium, and cultivated at 37° C. When the Klett value reached 170 to 200, IPTG was added thereto to give a final concentration of 0.4 mM, and the cultivation was further continued for 3 hours. Cells collected from 30 μl of the resulting culture solution were suspended in a sample buffer [50 mM Tris-HCl (pH 6.8), 2 mM EDTA, 1% SDS, 1% mercaptoethanol, 8% glycerol, 0.025% Bromophenol Blue], and heated for 5 minutes, followed by electrophoresis on 16% polyacrylamide gels containing 0.1% SDS. After electrophoresis, the gels were dyed with Coomassie Brilliant Blue. As a result, a 15-kilodalton (kDa) protein which was not detected in *E. coli* BL21 (DE3)/pET-3C obtained by transforming *E. coli* BL21 (DE3) by use of the above vector pET-3C was detected in *E. coli* BL21 (DE3)/pENGFT102. The amount of the 15 kDa protein produced was about 10% of the total protein. This protein was also detected by the Western blotting method using a rabbit anti-mouse NGF antibody (Collaborative Research, Inc. U.S.A.).

EXAMPLE 5

Construction of Polypeptide (I) Expression Vector for Animal Cells

A 1.1-kb EcoRI fragment containing the polypeptide (I) cDNA was isolated from the plasmid pHNT2 obtained in Example 2. The expression vector pTB389 (described in Japanese Patent Unexamined Publication (Laid-open) No. 64-2572/1989 corresponding to EP-251,244A) was similarly cleaved with EcoRI. The resulting fragment was ligated to the above 1.1-kb EcoRI fragment containing the polypeptide (I) cDNA with T4 DNA ligase, and then the ligation mixture was used for the transformation of *E. coli* DH1 (*Molecular Cloning A Laboratory Manual*, Cold Spring Harbor Laboratory, p.505, 1982). A plasmid was isolated from the resulting ampicillin-resistant transformant [*E. coli* DH1/pNTK26], and this plasmid was named pNTK26.

Figure 7:
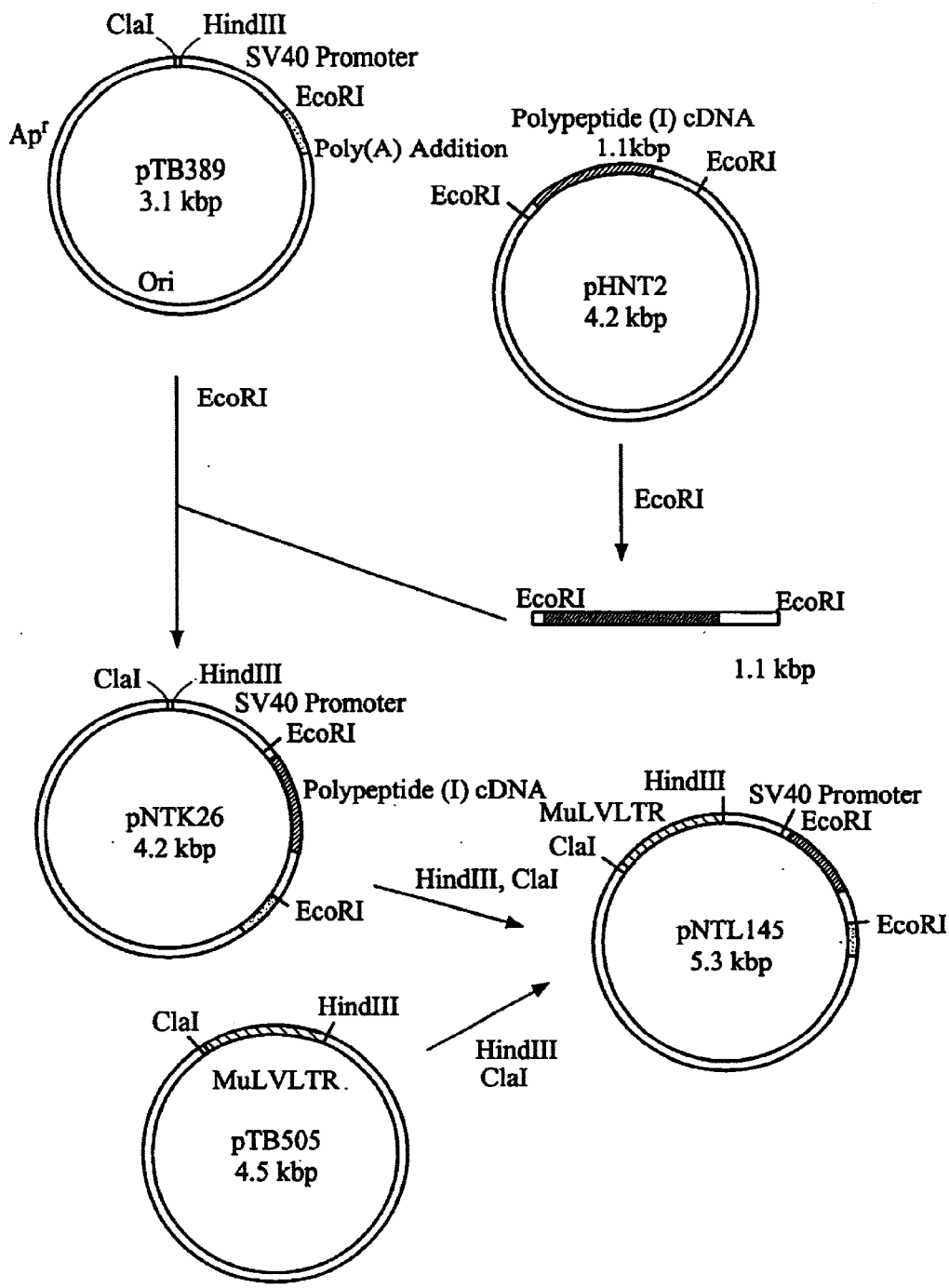
FIG. 7 is a schematic representation showing the construction of the polypeptide (I) expression vectors pNTK26 and pNTL145 for animal cells obtained in Example 5.

A 1.1-kb ClaI-HindIII fragment containing an Abelson mouse leukemia virus (A-MuLV) LTR region was isolated from plasmid pTB505 (described in Japanese Patent Unexamined Publication (Laid-open) No. 62-175182/1987 corresponding to EP-225,701A). The plasmid pNTK26 was similarly cleaved with restriction enzymes ClaI and HindIII, and the smaller fragment was removed. Then, the resulting fragment was ligated to the above 1.1-kb ClaI-HindIII fragment containing the A-MuLV LTR region with T4 DNA ligase, and the ligation mixture was used for the transformation of *E. coli* DH1 to give an ampicillin-resistant transformant *E. coli* DH1/pNTL145 (IFO 14873, FERM BP-2421). Plasmid pNTL145 was isolated from the transformant thus obtained (FIG. 7).

EXAMPLE 6

Construction of Polypeptide (I) Expression Vector for Animal Cells

A 0.83-kb EcoRI-AhaIII fragment containing the regions coding for the signal peptide, the propeptide and the polypeptide (I) in polypeptide (I) cDNA was isolated from the plasmid pHNT2 obtained in Example 2 (as to the location of the AhaIII site, refer to FIGS. 4 and 5). The 5'-terminus (EcoRI) of the resulting fragment was made flush with Klenow fragment, and then an XhoI linker pCCTCGAGG was ligated to each terminus thereof with T4 ligase, followed by treatment with XhoI. Thus, a 0.86-kb XhoI fragment was obtained.

Figure 8:
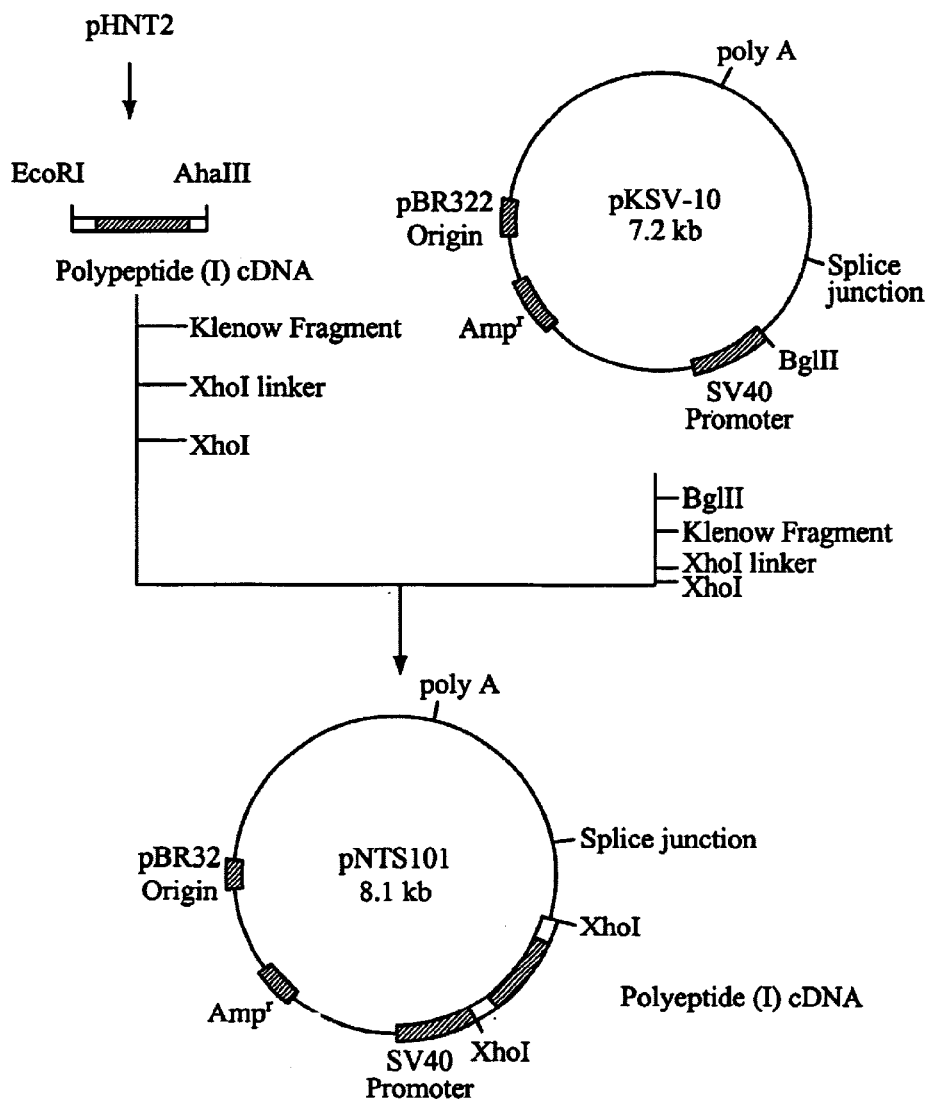
FIG. 8 is a schematic representation showing the construction of the polypeptide (I) expression vector pNTS101 for animal cells obtained in Example 6.

The expression vector pKSV-10 (Pharmacia) for animal cells was cleaved with restriction enzyme BglII, and then both ends (XhoI) of the resulting fragment were made flush with Klenow fragment. The XhoI linker (previously described) was added thereto, and this fragment was ligated to the above 0.86-kb XhoI fragment with T4 DNA ligase. The ligated fragment was used to transform *E. coli* DH1. Plasmid pNTS101 was isolated from the resulting ampicillin-resistant transformant *E. coli* DH1/pNTS101 (FIG. 8).

EXAMPLE 7

Expression of Polypeptide (I) cDNA in Animal Cells

Monkey COS-7 cells were cultivated in monolayer in Dulbecco's modified Eagle's medium (DMEM medium) (Flow Laboratories) containing 10% fetal calf serum, followed by exchanging the medium for the same medium. After 4 hours from the exchange, calcium phosphate gels containing the expression vector pTB389, 10 μg of the polypeptide (I) expression vector pNTK26 and the polypeptide (I) expression vector pNTL145, respectively, were prepared according to the known method [Graham et al., *Virology* 52, 456 (1973)], and added to cells to obtain transformants COS-7/pTB389, COS-7/pNTK26 and COS-7/pNTL145, respectively. These cells were cultivated in a carbon dioxide incubator for 4 hours, and then treated with glycerol [Gorman et al., *Science* 221, 551 (1983)], followed by cultivation for 3 days. Cultures after cultivation were centrifuged to obtain culture supernatants. PC12 cells were cultivated in the presence of the respective supernatants according to the method described in *Brain Research* 133, 350 (1977) and *Experimental Cell Research* 145, 179 (1983), and the proportions of cells whose neurites were more than 2 times the diameters of the cells were calculated. The results are shown in Table 2.

TABLE 2

| Vector | Culture Supernatant (μl) | Proportion of Cells with Neurites (%) |
| --- | --- | --- |
| pTB389 | 40 | 11 |
| pNTK26 | 40 | 17 |
| pNTL145 | 40 | 20 |

Using a culture supernatant obtained by a method similar to that described above, an effect on acetylcholine (ACh) content of co-cultured septal and basal forebrain neurons [M. Kakihana and M. Suno, *Nerve Chemistry* 27, 166 (1988)] was investigated.

Septum and basal forebrain were dissected from 17-day fetal brains, and nerve cells were isolated therefrom in accordance with the method of Hatanaka et al. [*Develop. Brain Res.* 30, 47 (1986)]. The cells were seeded on a 48-well plate pretreated with 100 μg/ml of poly-L-ornithine at a density of about $1 \times 10^6$ cells/cm$^2$/well, and cultivated in 500 μl of serum-free DME/F12/N2 medium for 24 hours. After removing by suction, 500 μl of DME/F12/10% FCS and the supernatant of the specimen were added. After 2 days, the culture solution was exchanged for 750 μl of the same culture solution, and the supernatant was added again, followed by cultivation for 2 days. The supernatant was added in two kinds of ways. Namely, 50 μl of the supernatant was added for the former two days and 75 μl thereof for the latter two days to give a final concentration of 10%. When mouse NGF (7S-NGF) purchased from Wako Junyaku was used, it was diluted with 0.1% ovalbumin/PBS, and 10 μl thereof was added.

After 4 days from the addition of the supernatant, the supernatant was removed by suction, and 500 μl of 0.3 N PCA cooled and 20 to 60 pmol/20 μl of EHC (ethylhomocholine) for measurement of ACh were added thereto. After gentle stirring, 500 μl of the solution was transferred to an Eppendolf microtube. Subsequent operations were carried out in accordance with previously reported methods, and the amount of ACh was measured by use of HPLC/ECD (high performance liquid chromatography/electrochemical detector system). After extraction of ACh, the cells were dissolved in 500 μl of 1N NaOH, and the amount of protein was determined (Bio-RAD protein assay). A Dunnett's t-test was used for statistical treatment.

The results are shown in Table 3.

17

TABLE 3

| Experiment | Sample | Number of Wells | Acetylcholine content (pmol/mg protein) |
|---|---|---|---|
| 1 | Mouse NGF 0 ng/ml | 6 | 492 ± 31 |
|  | Mouse NGF 0.1 ng/ml | 6 | 526 ± 14 |
|  | Mouse NGF 1 ng/ml | 6 | 600 ± 31 |
|  | Mouse NGF 10 ng/ml | 6 | 775 ± 29 |
|  | Supernatant (10%) of COS-7/pTB 389 | 6 | 582 ± 22 |
|  | Supernatant (10%) of COS-7/pNTL 145 | 6 | 652 ± 13 |
| 2 | Supernatant (10%) of COS-7/pTB389 | 4 | 332 ± 7 |
|  | Supernatant (10%) of COS-7/pNTL 145 | 6 | 395 ± 7 |

EXAMPLE 8

Construction of Polypeptide (I) Expression Vector for Yeast

Human lysozyme expression vector pGEL125 (produced by the method described in European Patent Publication No. 255,233) was cleaved with HindIII, and the resulting fragment was made flush with Klenow fragment, followed by ligation with T4 DNA ligase to obtain plasmid pGEL125H having no HindIII site. Then, the plasmid pGEL125H was cleaved with XhoI, and the resulting fragment was ligated to XhoI-HindIII adapter 5'TCGAGGCCACCGGTTCGA5' with T4DNA ligase, whereby an 8.3-kb HindIII-BamHI fragment was obtained. A 1.6-kb EcoRI fragment-containing α-factor gene was isolated from the plasmid p69A [Cell 30, 933 (1982)], and made flush with Klenow fragment. Thereafter, the resulting fragment was ligated to BamHI linker 5'CCGGATCCGG3' with T4 DNA ligase, followed by treatment with BamHI and HindIII. The 0.9-kb BamHI-HindIII fragment thus obtained (containing a promoter of the α-factor gene and a DNA coding for a prepro region) was ligated to the above 8.3-kb HindIII-BamHI fragment with T4 DNA ligase, and E. coli DH1 was transformed using this reaction mixture. A plasmid isolated from the resulting ampicillin-resistant transformant was named pALFA103 (9.2 kb).

The 0.9-kb BamHI-HindIII fragment containing the promoter of the α-factor gene and the DNA sequence coding for the prepro region was isolated and then inserted into phage vector M13mp18. In order to make a new HindIII site upstream from the 3'-terminus (HindIII site) of a DNA coding for a pro region of the α-factor by 24 bases, the codon TCT of serine at the 81st position in the pro region was converted to AGC. Namely, using primer 5'TTTATC-CAAGCTTACCCCTTC3' and the above phage vector M13mp18 containing the 0.9-kb BamHI-HindIII fragment, site-directed mutagenesis was conducted by use of an Amersham kit to obtain a desired clone. A 0.9-kb BamHI-HindIII fragment 24 bp shorter than that before the mutagenesis was isolated from the resulting clone, and ligated to the 8.3 kb BamHI-HindIII fragment (previously described) derived from pGEL125H to obtain plasmid pALFA310.

A 0.29-kb AhaIII-SalI fragment containing a PGK terminater was isolated from the plasmid pGLDp31-RcT (European Patent Publication No. 0235430). XhoI linker pCCTCGAGG was ligated to this fragment with T4 DNA ligase, followed by treatment with XhoI and SalI to obtain a 0.29-kb XhoI-SalI fragment containing the PGK terminater. This 0.29-kb XhoI-SalI fragment was inserted into an XhoI site positioned downstream from the DNA coding for the pro region of the α-factor in the plasmid pALFA 310 (previously described). Thus, plasmid pALFA 310T was obtained.

A 1.1-kb EcoRI fragment containing the polypeptide (I) cDNA was isolated from the plasmid pHNT2 obtained in Example 2. This 1.1-kb EcoRI fragment was cleaved with AhaIII, followed by addition of the XhoI linker. The resulting fragment was cleaved with ScaI to obtain a 0.36-kb ScaI-XhoI fragment. To this 0.36-kb ScaI-XhoI fragment was ligated the following synthetic DNA and the XhoI-HindIII adapter (previously described), followed by treatment with HindIII.

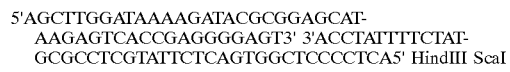

Thus, a 0.4-kb HindIII fragment coding for the polypeptide (I).

Figure 9:
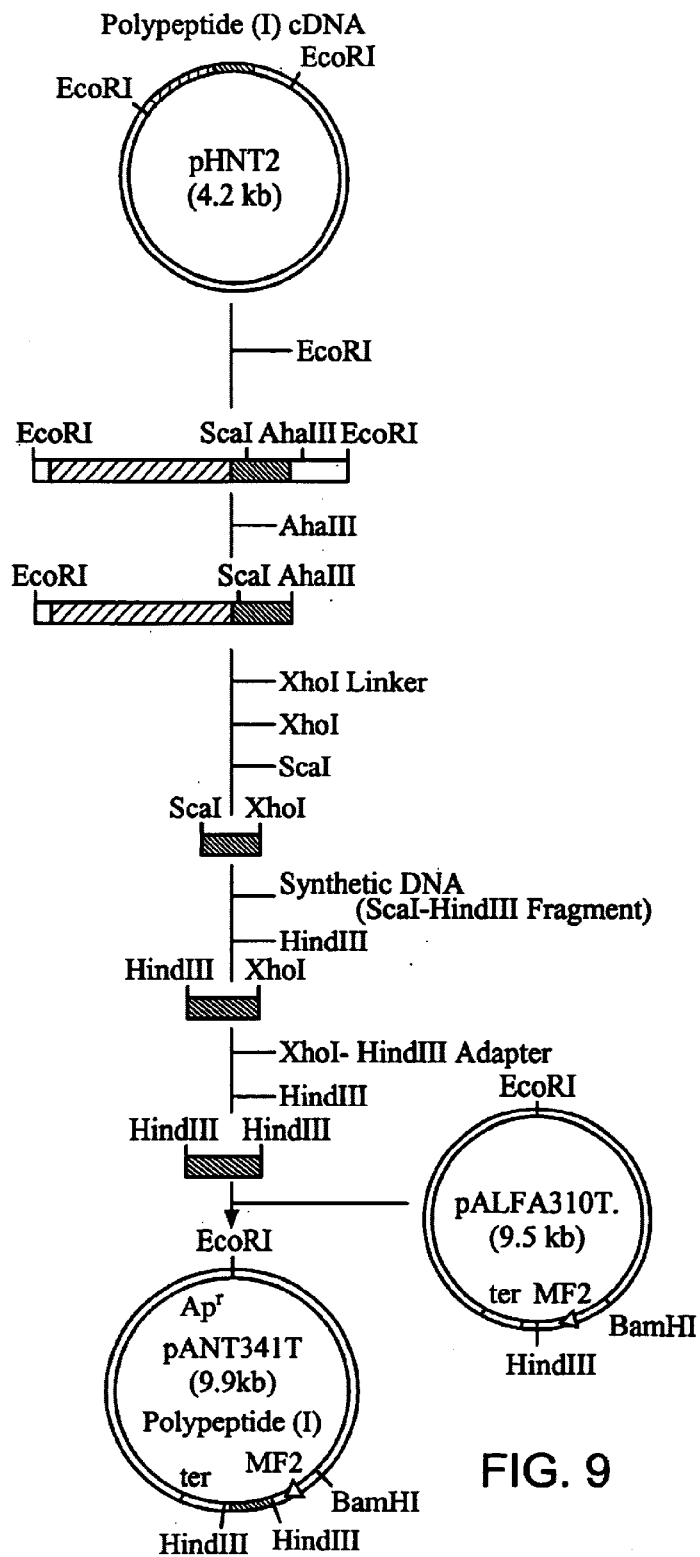
FIG. 9 is a schematic representation showing the construction of the polypeptide (I) expression vector pANT341T for yeast obtained in Example 8.

The 0.4-kb HindIII fragment coding for the polypeptide (I) was inserted into the HindIII site positioned at the 3'-terminus of the DNA coding for the prepro region of the α-factor of the plasmid pALFA310T, and thereby a polypeptide (I) expression vector pANT341T was obtained (FIG. 9).

EXAMPLE 9

Isolation of Transformant and Expression of Polypeptide (I) cDNA

Using the polypeptide (I) expression vector pANT341T obtained in Example 8, S. cerevisiae TB39 ƒ⁻ (IFO 10467, FERM BP-2399) obtained in Reference Example 1 was transformed by the lithium method [J. Bacterial. 153, 163 (1983)], whereby transformant S. cerevisiae TB39 ƒ⁻/pANT341T (IFO 10475, FERM BP-2530) was obtained.

The transformant S. cerevisiae TB39 ƒ⁻/pANT341T was inoculated into 5 ml of modified Burkholder medium (containing 89 g of sucrose, 11 g of glucose, 5.6 g of asparagine and 0.44 g of $KH_2PO_4$ per litter) [Amer. J. Bot. 30, 206 (1943)] in a test tube, and cultivated at 30° C. for 3 days with shaking. 1 ml of the resulting culture was transferred into a test tube containing 4 ml of the above medium, and cultivated at 30° C. for 1 day with shaking. 2 ml of this culture was further transferred into a 200-ml Erlenmeyer flask containing 18 ml of the above medium, and cultivated at 30° C. for 3 days with shaking.

The culture thus obtained was centrifuged, and trichloroacetic acid was added to 750 μl of its supernatant to precipitate proteins. The precipitate was dissolved in a sample buffer [Laemmli, Nature 227, 680 (1970)], and heated at 100° C. for 5 minutes, followed by electrophoresis on 15% polyacrylamide gels containing 0.5% SDS. The proteins on the gels were transferred to a nitrocellulose membrane according to the method of Burnette [Analytical Biochemistry 112, 195 (1981)].

Western blotting was carried out using a rabbit anti-mouse NGF antibody (Collaborative Research Inc. U.S.A.) and an affinity-purified HRP-linked goat anti-rabbit IgG (Bio RAD, U.S.A.). As a result, a band corresponding to a molecular weight of about 15 kilodaltons (kDa) of the polypeptide (I) was detected. On the other hand, for the supernatant of S. cerevisiae TB39 ƒ⁻/pALFA310T, this band was not detected.

EXAMPLE 10 production of Polypeptide (I) by E. coli

Escherichia coli BL21(DE3) (Gene 56, 125 (1987)] was transformed by use of the polypeptide (I) expression vector pENGFT102 obtained in Example 3 and T7 lysozyme expression vector pLysS to obtain transformant E. coli BL21/(DE3)/pLysS, pENGFT102 (IFO 14903, FERM BP-2529).

The transformant E. coli BL21 (DE3)/pLysS, pENGFT102 was cultivated in LB medium [1% tryptone (Difco), 0.5% yeast extract, 0.5% NaCl] containing 50 μg/ml of ampicillin, 10 μg/ml of chloramphenicol and 0.2% glucose at 37° C. for 16 hours with shaking. The culture (12.5 ml) was transferred into a 1-liter Erlenmeyer flask containing 250 ml of the same medium, and cultivated at 30° C. for 3 hours with shaking. Thereupon, the Klett value of the culture solution reached 170. Isopropyl-β-D(-)-thiogalactopyronoside was added to this culture at a final concentration of 0.1 mM, and the cultivation was continued at 30° C. for 3 hours with shaking. Cells collected from 30 μl of the culture thus obtained were suspended in 30 μl of sample buffer [Laemmli, Nature 227, 680 (1970)], and heated at 100° C. for 5 minutes, followed by electrophoresis on 16% polyacrylamide gels containing 0.1% SDS. The proteins on the gels were transferred to a nitrocellulose membrane according to the method of Burnette [*Analytical Biochemistry* 112, 195 (1981)], and then, Western blotting was carried out using the rabbit anti-mouse NGF antibody (Collaborative Research Inc. U.S.A.) and the affinity-purified HRP-linked goat anti-rabbit IgG (Bio RAD, U.S.A.). As a result, the polypeptide (I) having a molecular weight of 15 kilodaltons (kDa) was detected.

When gels obtained in a manner similar to that described above and subjected to electrophoresis were dyed with Coomassie Brilliant Blue, a 15-kDa protein corresponding to the polypeptide (I) was detected, and its production amount was estimated to be about 10% based on the total amount of proteins.

EXAMPLE 11

Isolation of Polypeptide (I)

The culture (3.75 liter) of the transformant E. coli BL21 (DE3)/pLysS, pENGFT102 obtained in Example 10 was centrifuged to give 17 g (wet) of cells. The cells were suspended in 375 ml of 50 mM Tris-HCl (pH 8.0) and freeze-thawed, followed by treatment with a sonic oscillator (Kaijo Denki, 2A, 2 minutes) 3 times. The broken cell suspension was centrifuged, and the resulting precipitate was dissolved in 60 ml of 5 M guanidine hydrochloride-5 mM EDTA-1 mM PMSF-0.1 mM APMSF-20 mM dithiothreitol (DTT)-50 mM sodium phosphate buffer (pH 6.0). The solution thus obtained was applied to a Sephacryl S-200 column equilibrated with 2 M guanidine hydrochloride-5 mM EDTA-0.1 mM APMSF-5 mM DTT-25 mM sodium phosphate buffer (pH 6.0), and the fractions in which the polypeptide (I) was detected by the Western blotting method (previously described) were collected (volume=300 ml). This solution was concentrated by use of an ultrafilter equipped with a YM5 membrane (Amicon), and 50 ml of the resulting concentrated solution was applied to the Sephacryl S-200 column as described above. Thus, 164 ml of a solution containing 328 mg of the purified polypeptide (I) was obtained. The purity was investigated by SDS-polyacrylamide gel electrophoresis. As a result, it was confirmed that the resulting purified polypeptide (I) was substantially homogeneous.

A solution containing the above purified polypeptide (I) was loaded onto an Ultrapore RPSC column (0.46×7.5 cm, Altex), and chromatographed by high-performance liquid chromatography (HPLC) with a trifluoroacetic acid-acetonitrile eluent solvent system to obtain the homogeneous polypeptide (I). The N-terminal amino acid sequence of the resulting polypeptide (I) was determined with a gas phase protein sequencer (Model 470A, Applied Biosystems). Consequently, the N-terminal amino acid sequence of the purified polypeptide (I) agreed with the N-terminal amino acid sequence of the polypeptide (I) deduced from the nucleotide sequence of cDNA except that a methionine residue was added to the N-terminus (Table 4).

TABLE 4

| | N-terminal Amino Acid Sequence | | | | | | | | | |
|---|---|---|---|---|---|---|---|---|---|---|
| | 1 | 2 | 3 | 4 | 5 | 6 | 7 | 8 | 9 | 10 |
| Sequence Determined from Purified Sample | Met | Tyr | Ala | Glu | His | Lys | Ser | His | Arg | Gly |
| Sequence Deduced from cDNA | Tyr | Ala | Glu | His | Lys | Ser | His | Arg | Gly | Glu |

The amino acid composition of the purified sample obtained above was determined by the ninhydrin method. As a result, the observed values substantially agreed with the theoretical values calculated from the polypeptide (I) to the N-terminus of which a methionine residue was added (Table 5).

TABLE 5

| | Amino Acid Composition | |
|---|---|---|
| | Experimental[1] Value | Theoretical[2] Value |
| Asp | 10.3 | 11 |
| Thr | 8.3 | 9 |
| Ser | 10.0 | 12 |
| Glu | 11.0 | 11 |
| Pro | 1.8 | 2 |
| Gly | 7.9 | 8 |
| Ala | 5.1 | 5 |
| Cys | 5.9 | 6 |
| Val | 8.4 | 9 |
| Met | 1.0 | 1 |
| Ile | 6.8 | 7 |
| Leu | 5.1 | 5 |
| Tyr | 5.2 | 5 |
| Phe | 1.1 | 1 |
| Lys | 9.6 | 10 |
| His | 3.6 | 4 |
| Arg | 9.3 | 10 |
| Trp | 3.6 | 4 |

[1]Calculated taking Glu as 11.

TABLE 5-continued

Amino Acid Composition

| Experimental[1] Value | Theoretical[2] Value |
|---|---|

[2]Calculated with a methionine residue was added to the N-terminus of the polypeptide (I).

A solution (protein concentration: 2 mg/ml) containing the above purified polypeptide (I) was diluted with 2 M guanidine hydrochloride-5 mM EDTA-0.1 mM APMSF-5 mM DTT-25 mM sodium phosphate buffer (pH 6.0) so as to give a protein concentration of 10 µg/ml. The diluted solution was dialyzed against a 50-fold amount of 1 mM EDTA-50 mM NaHCO$_3$-Na$_2$Co$_3$ (pH 10.0) at 4° C. for 16 hours and further dialyzed against the same buffer for 4 hours. The effect of the resulting dialyzed fluid on PC12 cells was examined in accordance with the method described in *Brain Research* 133. 350 (1979) and *Experimental Cell Research* 145, 179 (1983). As a result, it was observed that 6% of the PC12 cells had neurites by addition of the inner dialyzed fluid, and 2% thereof had neurites having a length of at least 2 times the diameter of the cell body. On the other hand, for 1 mM EDTA-50 mM NaHCO$_3$-Na$_2$Co$_3$ (pH 10.0) as a control, not more than 0.5% of the cells had neurites. It was observed that the purified polypeptide (I) obtained by a method similar to that described above had the activity (previously described) of promoting the survival of chicken embryo sensory neurons (dorsal root ganglia).

EXAMPLE 12

Expression of Polypeptide (I) cDNA in Animal Cells

Monkey COS-7 cells were cultivated in monolayer in Dulbecco's modified Eagle's medium (DMEM medium) containing 10% fetal calf serum in a carbon dioxide incubator, followed by exchanging the medium for the same medium. After 4 hours from the exchange, calcium phosphate gels containing 10 µg of pTB389 (described in Japanese Patent Unexamined Publication (Laid-open) No. 64-2572/1989 corresponding to EP-251,244A) or 10 µg of pNTL145 (refer to Example 5) were prepared according to a known method [Graham et al., *Virology* 52, 456 (1973)], and added to cells. These cells were cultivated for 4 hours, and then treated with glycerol [Gorman et al., *Science* 221, 551 (1983)], followed by cultivation in DMEM containing 10% fetal calf serum for 16 hours. After the medium was exchanged for DMEN containing 0.5% fetal calf serum, the cells were further cultivated for 2 days, and the resulting culture was centrifuged. The thus obtained culture supernatant (sample 1) of the COS-7 cells transfected with pTB389 and the culture supernatant (sample 2) of the COS-7 cells transfected with pNTL145 were used for the following experiments.

Trichloroacetic acid was added to 0.5 ml of each sample to precipitate proteins. The resulting precipitate was dissolved in a sample buffer [Laemmli, *Nature* 227, 680 (1970)], and heated at 100° C. for 5 minutes, followed by electrophoresis on 17% polyacrylamide gels containing 0.5% SDS. The proteins on the gels were transferred to a nitrocellulose membrane according to the method of Burnette [*Analytical Biochemistry* 112, 195 (1981)]. Western blotting was carried out using the anti-polypeptide (I) N-terminal peptide antibody obtained in Reference Example 2 and affinity-purified HRP-linked goat anti-rabbit IgG (Bio RAD, U.S.A.). As a result, for the culture supernatant (sample 2) of the COS-7 cells transfected with pNTL145, a band of molecular weight of about 15 kilodaltons (kDa) corresponding to polypeptide (I) was detected. However, for the culture supernatant (sample 1) of the COS-7 cells transfected with pTB389, the band corresponding to the polypeptide (I) was not detected. When an anti-mouse NGF antibody (Collaborative Research, U.S.A.) was used in place of the above anti-polypeptide (I) N-terminal peptide antibody, the band corresponding to the polypeptide (I) was detected.

Sensory neurons (dorsal root ganglia) were isolated from 8-day-old chicken embryos and treated with 0.1% trypsin (swine pancreas crystallized trypsin, Wako Junyaku) in CMF (calcium-magnesium free)-PBS at 37° C. for 20 minutes to disperse cells. The pre-cultivation of the cells was performed in DMEM containing 10% fetal calf serum (FCS) on a plastic culture dish for 2 hours, and thereby non-nerve cells were adhered. Then, cells not adhered were collected by centrifugation, and seeded on a 24-well plate coated with poly-L-ornithine at a density of $10^4$ to $10^5$ cells/well. Each sample dialyzed against DMEM was immediately added thereto for cultivation, using a mixture culture medium (DMEM containing 10% FCS, 1 µM Ara-C and 50 µg/ml of kanamycin:Ham's F12 =1:1) as a culture medium. After cultivation for 4 days, the numbers of surviving nerve cells were determined with respect to 10 visual fields per well, on the scale that the cell had a smooth surface and a neurite with a length of at least 2 times the diameter of the cell body.

The configurations of the nerve cells were compared to one another, 3 days after the cultivation was initiated.

When $10^5$ cells were placed in each well and each sample was added thereto in an amount of 10% by volume, based on the culture solution, in the sample 2, a number of surviving nerve cells were observed and neurites were densely distributed. In contrast, in the sample 1, a number of dead cells (floating cells having uneven contours and no neurites) were observed and the surviving cells were smaller in number than that in the example 2.

When the cells seeded at a density of $10^4$ cells/well were cultivated, all samples exhibited the high development of the neurites in sample concentrations of 5% and 10%. However, in a sample concentration of 2%, the nerve cells having highly developed neurites were observed in the sample 2, whereas the development of the neurites was poor and the cell bodies were small in the sample 1.

Figure 10:
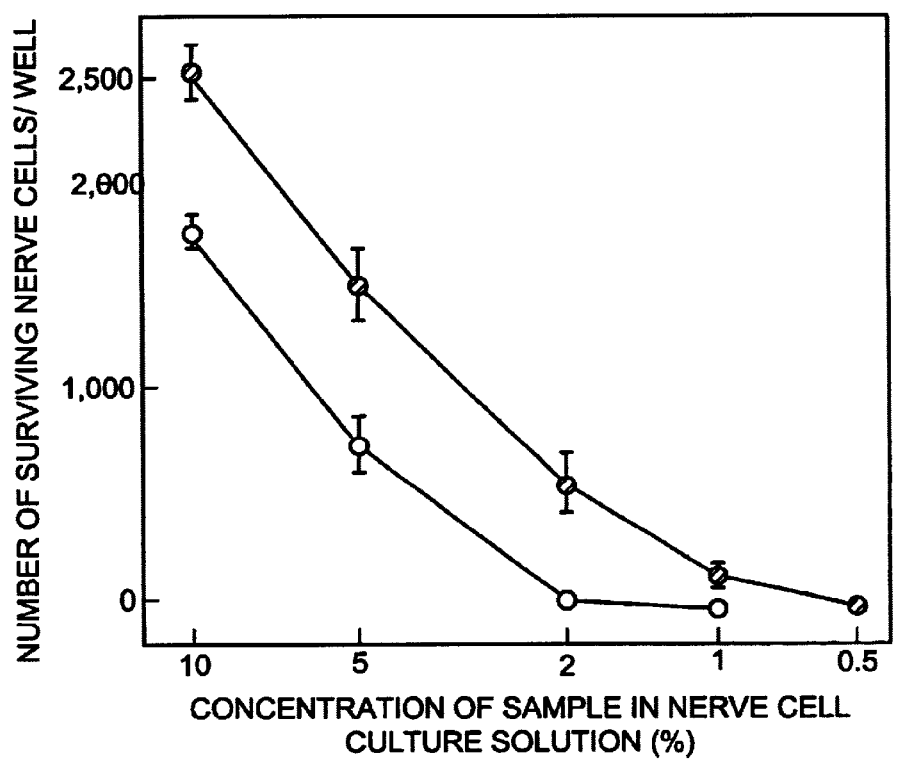
FIG. 10 is a graph showing the influence of each sample on the survival of chicken embryo sensory nerve cells obtained in Example 12.

When the cells seeded at a density of $10^4$ cells/well were cultivated, the number of the surviving nerve cells was counted, 4 days after the cultivation was initiated (FIG. 10). Referring to FIG. 10, open circles (○) show the culture supernatant (sample 1) of the COS-7 cells transfected with pTB389, and closed circles (●) show the culture supernatant (sample 2) of the COS-7 cells transfected with pNTL145. The sample 2 increased the survival of the sensory nerve cells and its effect was dependent on concentration, compared to the sample 1.

EXAMPLE 13

Cloning of Rat Polypeptide (I) Gene

A 1.1-kb EcoRI DNA fragment containing polypeptide (I) cDNA was isolated from the plasmid pHNT2 obtained in Example 2, and labelled by the oligolabelling reaction (Nippon Gene) to obtain a probe.

Total RNA was prepared from each organ of 5-week-old rats by the Guanidium-CsCl method, and poly(A) RNA was obtained by use of oligo-dt cellulose. Using the probe described above, Northern blotting of the poly(A) RNA obtained from each tissue was carried out. Consequently, a 1.4-kb messenger RNA (mRNA) of polypeptide (I) was detected in the kindney, liver, heart, brain, spleen, thymus, lung and submandibular gland. The above result suggested that the polypeptide (I) gene also existed in rat and was expressed in many tissues.

A 0.45-kb EcoRI-AhaIII fragment coding for the human polypeptide (I) was isolated from the plasmid pUNK5 obtained in Example 1, and Southern hybridization of rat genomic DNA was carried out using this fragment as a probe. This probe hybridized to an approximately 7.4-kb EcoRI fragment, an approximately 3.8-kb BglII fragment and an approximately 3.8-kb HindIII fragment, and this suggested that a polypeptide (I) gene also existed in rat.

Then, a 1.1-kb EcoRI fragment containing polypeptide (I) CDNA was isolated from the plasmid pHNT2 obtained in Example 2, and the rat polypeptide (I) gene was cloned using this fragment as a probe. A rat genomic DNA library used for cloning, which was constructed by partially digesting DNA derived from liver of female rat (Sprague-Dawley) and introducing the regulting fragment into a Charon 4A phage, was purchased from Clontech. *E. coli* LE362 was infected with this phage library to form about 5×10$^5$ plaques per plate. The phage DNAs were transferred from 10 independent plates to a nitrocellulose membrane according to the known method [T. Maniatis et al., *Molecular Cloning, A Laboratory Manual*], and hybridized with the above probe. As a result, 7 positive clones were obtained. One positive clone (λrNGF2-8) contained an approximately 12-kb inserted DNA fragment. It was deduced from the results of the Southern hybridization that a region coding for the polypeptide (I) existed in a 0.95-kb BglII-HindIII fragment in the DNA fragment. Then, the 0.95-kb BglII-HindIII fragment was subcloned in plasmid pUC118 (Takara Shuzo) to obtain plasmid pRNT18. Using the plasmid pRNT18, *E. coli* DH1 was transformed to obtain transformant *E. coli* DH1/pRNT18 (IFO 14934, FERM BP-2618).

The above 0.95-kb BglII-HindIII fragment was cleaved with various restriction enzymes, and the resulting fragments were subcloned in pUC118, M13mp18 and the like, respectively. Then, their nucleotide sequences were determined by use of Seaqunase (Toyobo) (FIG. 11). Consequently, it was revealed that the 0.95-kb BglII-HindIII fragment contained a region coding for a signal peptide, a pro region and a mature protein of the rat polypeptide (1), and that an intron did not exist.

Comparing the amino acid sequence of the rat polypeptide (I) deduced from the nucleotide sequence to that of the human polypeptide (I), differences were observed at 11 residues for the signal sequence and the pro region, but there was no difference for the mature protein (polypeptide (I)). It was thus proved that the amino acid sequence of the rat polypeptide (I) completely agreed with that of the human polypeptide (I).

EXAMPLE 14

Cloning of Polypeptide (I) cDNA

A 0.83-kb DNA fragment coding for a signal sequence, a pro region and.a polypeptide (I) was isolated from polypeptide (I) cDNA to prepare a probe. Using the resulting probe, 0.73-kb and 1.1-kb polypeptide (I) cDNAs, were cloned from a human placenta library (Clontech Laboratories, Inc.) in a manner similar to those in Examples 1 and 2. The nucleotide sequence of the polypeptide (I) cDNA thus obtained agreed with the nucleotide sequence of the polypeptide (I) cDNAs cloned in Examples 1 and 2.

EXAMPLE 15

Establishment of Polypeptide (I)-Producing Animal Cell Strain by Introduction of Polypeptide (I) Expression Vector (1) Construction of Expression Vector A 0.86-kb EcoRI-AhaIII fragment containing regions coding for a signal peptide, a propeptide and a polypeptide (I) of the polypeptide (I) CDNA was isolated from the plasmid pHNT2 obtained in Example 2. On the other hand, the plasmid pTB399 [*Cell Struct. Funct.* 12, 205 (1987)] for expression of interleukin (IL)-cDNA was cleaved with BglII, and then treated with DNA polymerase Klenow fragment, followed by further cleavage with EcoRI to obtain a fragment (about 3.8 kb) from which the IL-cDNA portion was removed. To this fragment was ligated the above 0.86-kb EcoRI-AhaIII fragment by the T4 DNA ligase reaction to obtain plasmid pTB1091.

Figure 12:
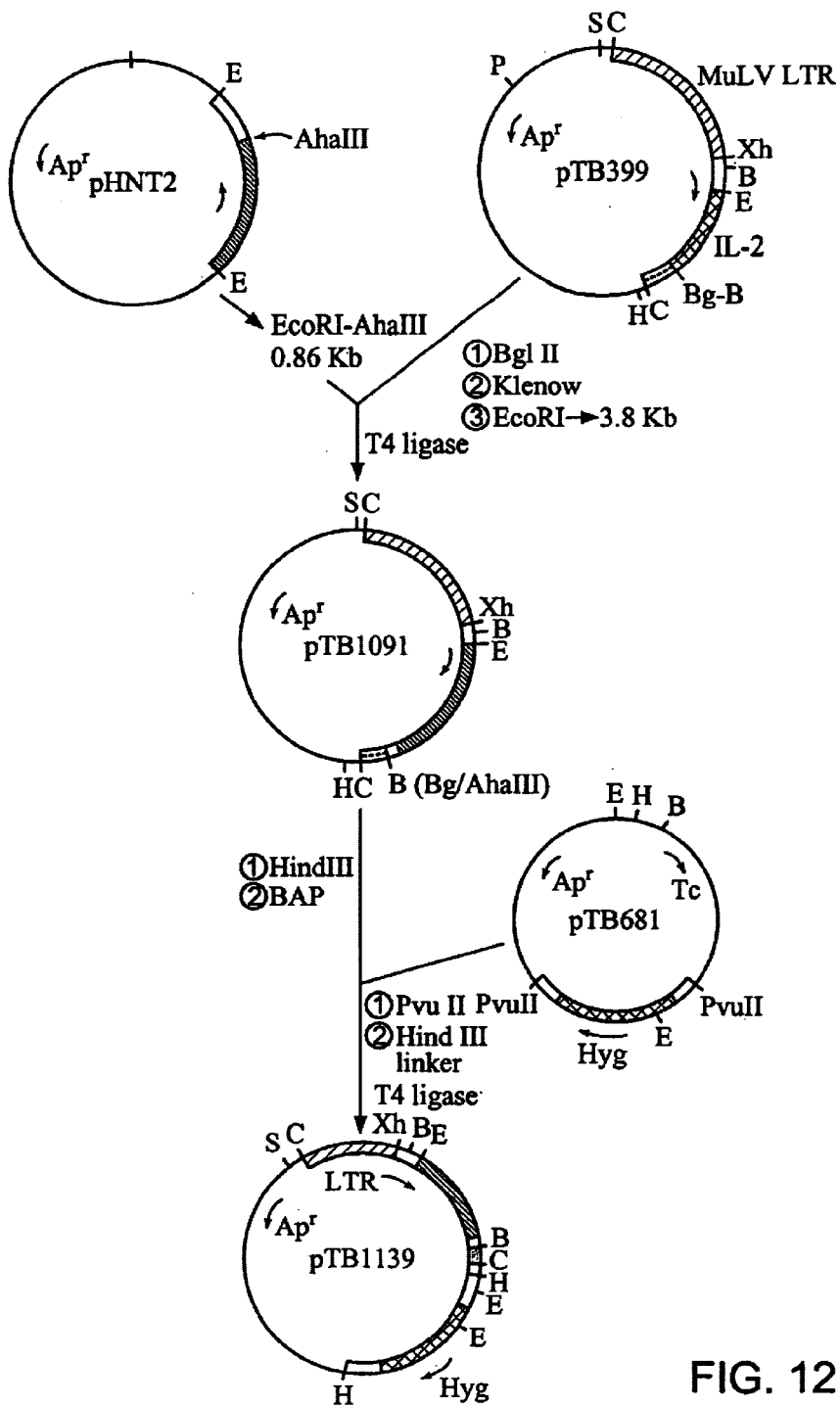
FIG. 12 is a schematic representation showing the construction of the polypeptide (I) expression vector pTB1139 obtained in Example 15.

Then, a 1.0-kb BamHI fragment containing a hygromycin B-resistant gene was isolated from plasmid pLG89 [*Gene* 25, 179 (1983)], and replaced with a region (1.0-kb BglII-SmaI) containing the neomycin-resistant gene of pTB6 [*Cell Struct. Funct.* 12, 205 (1987)]. Thus, the hygromycin-resistant gene expression vector pTB681 having an HSV TK gene promoter was constructed. A HindIII linker was added to a 1.8-kb fragment obtained by cleaving the plasmid pTB681 with PvuII, and then the resulting fragment was inserted into the HindIII site of the polypeptide (I) expression vector pTB1091 obtained above to construct the polypeptide (I) expression vector pTB1139 having the hygromycin-resistant gene (FIG. 12).

(2) Establishment of Polypeptide (I)-Producing Animal Cell Strain

Mouse L cells (TK-deficient strain) were seeded on a Falcon Schale 6 cm in diameter (7×10$^5$ cells/Schale), and cultivated in Eagle's MEM containing 10% FCS. The next day, the cells were transfected with 10 μg of the expression vector pTB1139 in accordance with the method of Graham et al. [*Virology* 52, 456 (1973)], followed by cultivation in the above medium for 2 days. After treatment with trypsin, the resulting cells were seeded on a new Schale again, and the cultivation was continued in 10% FCS-MEM containing 500 μg/ml of hygromycin B(Sigma). After 2 to 3 weeks, hygromycin-resistant cells multiplied in a colony form were obtained. The hygromycin-resistant L cells thus obtained were cloned according to a known method such as the limited dilution method to obtain clones L-H1-1, L-H6-1, L-H11-1, L-H13-1, L-H14-1 (IFO 50223, FERM BP-2754), L-H18-1, L-H19-1, L-H35-1, L-H36-1 and L-H43-1. The cells of each clone were seeded on a 24-well plate and cultivated. When the cells became approximately confluent, the medium was exchanged for 0.5 ml/well of MEM medium containing 0.1% FCS.

After the cultivation for 2 days, a supernatant was subjected to SDS-polyacrylamide gel electrophoresis, and the polypeptide (I) was detected by Western blotting using the polypeptide (I) N-terminal peptide antibody prepared in Reference Example 2. As a result, it was revealed that about 1 mg of the polypeptide (I) was produced in the medium of each clone described above.

The following references, which are referred to for their disclosures at various points in this application, are incorporated herein by reference.

Biochemistry 18, 5294 (1979)
Molecular and Cellular Biology 2, 161 (1979)
Molecular and Cellular Biology 3, 280 (1983)
Gene 25, 263 (1983)
Gene 2, 95 (1977)
Gene 4, 121 (1978)
Gene 19, 259 (1982)
Gene 33, 103 (1985)
Methods in Enzymology 153, 3 (1987)
Proc. Natl. Acad. Sci. U.S.A. 80, 1194 (1983)
Molecular Cloning, A Laboratory Manual, Cold Spring Harbor Laboratory, p.239 (1982)
DNA Cloning, A Practical Approach 1, 49 (1985)
Proc. Natl. Acad. Sci. U.S.A. 60, 160 (1968)
Nucl. Acids Res. 9, 309 (1981)
Journal of Molecular Biology 120, 517 (1978)
Journal of Molecular Biology 41, 459 (1969)
Genetics 39, 440 (1954)
Molecular Cloning, Cold Spring Harbor Laboratory, p.249 (1982)
Proc. Natl. Acad. Sci. U.S.A. 68, 2417 (1971)
Nature 302, 538 (1983)
Nature 303, 821 (1983)
Proc. Natl. Acad. Sci. U.S.A. 74, 560 (1977)
Nucleic Acids Research 9, 309 (1981)
Proc. Natl. Acad. Sci. U.S.A. 69, 2110 (1972)
Molecular & General Genetics 168, 111 (1979)
J. Mol. Biol. 56, 209 (1971)
J. Bacteriol. 156, 1130 (1983)
Proc. Natl. Acad. Sci. U.S.A. 75, 1929 (1978)
J. Bacteriol. 153, 163 (1983)
Virology 52, 456 (1973)
Journal of Experiments in Molecular Genetics, 431–433, Cold Spring Harbor Laboratory, New York, (1972)
Proc. Natl. Acad. Sci. U.S.A., 77, 4505 (1980)
Science 122, 501 (1952)
Virology 8, 396 (1959)
J. Am. Med. Assoc. 199, 519 (1967)
Proc. Soc. Exp. Biol. Med. 73, 1 (1950)
Brain Research 133, 350 (1977)
Experimental Cell Research 145, 179 (1983)
Developmental Biology 111, 62 (1985)
Molecular and Cellular Biology 4, 771 (1984)
Adv. Enzymol. 32, 221–296 (1969)
Arch. Biochem. Biophys. 82, 70–77 (1959)
Gene 56, 125 (1987)
Japanese Patent Unexamined Publication (Laid-open) No. 62-175182/1987 corresponding to EP-225,701A)
Science 221, 551 (1983)
Experimental Cell Research 145, 179 (1983)
Nerve Chemistry 27, 166 (1988)
Develop. Brain Res. 30, 47 (1986)
European Patent Publication No. 255,233
Cell 30, 933 (1982)
Amer. J. Bot. 30, 206 (1943)
Nature 227, 680 (1970)
Analytical Biochemistry 112, 195 (1981)
Experimental Cell Research 145, 179 (1983)
Japanese Patent Unexamined Publication (Laid-open) No. 64-2572/1989 corresponding to EP-251,244A
Cell Struct. Funct. 12, 205 (1987)

What is claimed is:

1. A substantially pure polypeptide comprising the following amino acid sequence (II), (N) TyrAlaGluHisLysSerHisArgGlyGluTyrSerValCys AspSerGluSerLeuTrpValThrAspLysSerSerAlaIle AspIleArgGlyHisGlnValThrValLeuGlyGluIleLys Thr-GlyAsnSerProValLysGlnTyrPheTyrGluThrArg CysLysGluAlaArgProValLysAsnGlyCysArgGlyIle AspAspLysHisTrpAsnSerGlnCysLysThrSerGlnThr TyrValArgAlaLeuThrSerGluAsnAsnLysLeuValGly TrpArgTrpIleArgIleAspThrSerCysValCysAlaLeu SerArgLysIleGlyArg(C) (II).

wherein the polypeptide has the functions of promoting the differentiation and growth of animal cells, promoting the survival of animal cells, enhancing gene expression, or inducing the production of proteins and enzymes.

2. The polypeptide according to claim 1, which has the following amino acid sequence (II'):

(N) TyrAlaGluHisLysSerHisArgGlyGluTyrSerValCys AspSerGluSerLeuTrpValThrAspLysSerSerAlaIle AspIleArgGlyHisGlnValThrValLeuGlyGluIleLys Thr-GlyAsnSerProValLysGlnTyrPheTyrGluThrArg CysLysGluAlaArgProValLysAsnGlyCysArgGlyIle AspAspLysHisTrpAsnSerGlnCysLysThrSerGlnThr TyrValArgAlaLeuThrSerGluAsnAsnLysLeuValGly TrpArgTrpIleArgIleAspThrSerCysValCysAlaLeu SerArgLysIleGlyArgThr (II').

3. A recombinant DNA coding for a polypeptide comprising the following amino acid sequence (II):

(N) TyrAlaGluHisLysSerHisArgGlyGluTyrSerValCys AspSerGluSerLeuTrpValThrAspLysSerSerAlaIle AspIleArgGlyHisGlnValThrValLeuGlyGluIleLys Thr-GlyAsnSerProValLysGlnTyrPheTyrGluThrArg CysLysGluAlaArgProValLysAsnGlyCysArgGlyIle AspAspLysHisTrpAsnSerGlnCysLysThrSerGlnThr TyrValArgAlaLeuThrSerGluAsnAsnLysLeuValGly TrpArgTrpIleArgIleAspThrSerCysValCysAlaLeu SerArgLysIleGlyArg (II).

4. A vector including a DNA coding for a polypeptide comprising the following amino acid sequence (II):

(N) TyrAlaGluHisLysSerHisArgGlyGluTyrSerValCys AspSerGluSerLeuTrpValThrAspLysSerSerAlaIle AspIleArgGlyHisGlnValThrValLeuGlyGluIleLys Thr-GlyAsnSerProValLysGlnTyrPheTyrGluThrArg CysLysGluAlaArgProValLysAsnGlyCysArgGlyIle AspAspLysHisTrpAsnSerGlnCysLysThrSerGlnThr TyrValArgAlaLeuThrSerGluAsnAsnLysLeuValGly TrpArgTrpIleArgIleAspThrsercysValcysAlaLeu SerArgLysIleGlyArg (II).

5. A host cell transformed by a vector including a DNA coding for a polypeptide comprising the following amino acid sequence (II):

(N) TyrAlaGluHisLysSerHisArgGlyGluTyrSerValCys AspSerGluSerLeuTrpValThrAspLysSerSerAlaIle AspIleArgGlyHisGlnValThrvalLeuGlyGluIleLys Thr-GlyAsnSerProValLysGlnTyrPheTyrGluThrArg CysLysGluAlaArgProValLysAsnGlyCysArgGlyIle AspAspLysHisTrpAsnSerGlnCysLysThrSerGlnThr TyrValArgAlaLeuThrSerGluAsnAsnLysLeuValGly TrpArgTrpIleArgIleAspThrSerCysValCysAlaLeu SerArgLysIleGlyArg (II).

6. *Escherichia coli* BL21(DE3)/pENGFT102 (FERM BP-2420) according to claim 5.

7. *Saccharomyces cerevisiae* TB39 $\rho^{31}$/pANT341T (FERM BP-2530) according to claim 5.

8. *Escherichia coli* BL21(DE3)/pLysS, pENGFT102 (FERM BP-2529) according to claim 5.

9. L-H14-1 (FERM BP-2754) according to claim 5.

10. A process for producing a polypeptide (I) comprising the following amino acid sequence (II):

TyrAlaGluHisLysSerHisArgGlyGluTyrSerValCys AspSerGluSerLeuTrpValThrAspLysSerSerAlaIle AspIle-

ArgGlyHisGlnValThrValLeuGlyGluIleLys ThrGlyAsnSerProValLysGlnTyrPheTyrGluThrArg CysLysGluAlaArgProValLysAsnGlyCysArgGlyIle AspAspLysHisTrpAsnSerGlnCysLysThrSerGlnThr TyrValArgAlaLeuThrSerGluAsnAsnLysLeuValGly TrpArgTrpIleArgIleAspThrSerCysValCysAlaLeu SerArgLysIleGlyArg (C)(II).

which comprises cultivating a host cell transformed by a vector including a DNA coding for the polypeptide in a culture medium;

accumulating the polypeptide; and collecting the polypeptide.

11. A purified polypeptide having an amino acid sequence as follows:

(N) MetTyrAlaGluHisLysSerHisArgGlyGluTyrSerValCys AspSerGluSerLeuTrpValThrAspLysSerSerAlaIle AspIleArgGlyHisGlnValThrValLeuGlyGluIleLys
ThrGlyAsnSerProValLysGlnTyrPheTyrGluThrArg CysLysGluAlaArgProValLysAsnGlyCysArgGlyIle AspAspLysHisTrpAsnSerGlnCysLysThrSerGlnThr TyrValArgAlaLeuThrSerGluAsnAsnLysLeuValGly TrpArgTrpIleArgIleAspThrSerCysValCysAlaLeu SerArgLysIleGlyArgThr(C).

12. An isolated nucleic acid comprising a nucleotide sequence encoding a polypeptide having an amino acid sequence as follows:

(N) MetTyrAlaGluHisLysSerHisArgGlyGluTyrSerValCys AspSerGluSerLeuTrpValThrAspLysSerSerAlaIle AspIleArgGlyHisGlnValThrValLeuGlyGluIleLys
ThrGlyAsnSerProvalLysGlnTyrPheTyrGluThrArg CysLysGluAlaArgProValLysAsnGlyCysArgGlyIle AspAspLysHisTrpAsnSerGlnCysLysThrSerGlnThr TyrValArgAlaLeuThrSerGluAsnAsnLysLeuValGly TrpArgTrpIleArgIleAspThrSerCysValCysAlaLeu SerArgLysIleGlyArgThr(C).

13. A vector comprising the nucleotide sequence of claim 12.

14. The vector of claim 13 which is an expression vector.

15. A host cell comprising the nucleotide sequence of claim 12.

16. The host cell of claim 15 which is bacterium.

17. The host cell of claim 16 which is *E. coli*.

18. The host cell of claim 15 which is actinomycetes, yeast, mold, insect or animal cell.

19. A host cell transformed with the vector of claim 14, or progeny thereof.

20. The host cell of claim 19 which is a bacterium.

21. The host cell of claim 20 which is *E. coli*.

22. The host cell of claim 19 which is actinomycetes, yeast, mold, insect or animal cell.

23. A method for producing the purified polypeptide of claim 1, said method comprising:

(a) culturing a host cell comprising a nucleotide sequence encoding said polypeptide such that said host cell produces said polypeptide; and (b) purifying said polypeptide.

24. The method of claim 23 wherein said host cell is a bacterium.

25. The method of claim 24, wherein said host cell is *E. coli*.

* * * * *